(12) United States Patent
Claude et al.

(10) Patent No.: US 11,642,523 B2
(45) Date of Patent: May 9, 2023

(54) SINUS TREATMENT DEVICE WITH ENHANCED TIP

(71) Applicant: TIVIC HEALTH SYSTEMS INC., Menlo Park, CA (US)

(72) Inventors: John Claude, Redwood City, CA (US); Christopher A. Wiklof, Everett, WA (US)

(73) Assignee: Tivic Health Systems Inc., Menlo Park, CA (US)

( * ) Notice: Subject to any disclaimer, the term of this patent is extended or adjusted under 35 U.S.C. 154(b) by 20 days.

(21) Appl. No.: 16/664,061

(22) Filed: Oct. 25, 2019

(65) Prior Publication Data

US 2020/0164202 A1 May 28, 2020
US 2021/0196945 A9 Jul. 1, 2021

Related U.S. Application Data

(63) Continuation-in-part of application No. PCT/US2018/029030, filed on Apr. 24, 2018.
(Continued)

(51) Int. Cl.
| | | |
|---|---|---|
| *A61N 1/36* | (2006.01) | |
| *A61B 5/053* | (2021.01) | |
| *A61N 1/04* | (2006.01) | |
| *A61N 1/02* | (2006.01) | |
| *A61N 1/08* | (2006.01) | |
| *A61N 1/20* | (2006.01) | |
| *A61B 5/00* | (2006.01) | |

(Continued)

(52) U.S. Cl.
CPC .......... *A61N 1/36031* (2017.08); *A61B 5/053* (2013.01); *A61N 1/02* (2013.01); *A61N 1/025* (2013.01); *A61N 1/04* (2013.01); *A61N 1/0428* (2013.01); *A61N 1/0456* (2013.01); *A61N 1/0472* (2013.01); *A61N 1/08* (2013.01); *A61N 1/205* (2013.01); *A61N 1/36* (2013.01); *A61N 1/3601* (2013.01); *A61N 1/36014* (2013.01); *A61N 1/36021* (2013.01); *A61N 1/36034* (2017.08); *A61B 5/6814* (2013.01); *A61B 5/7225* (2013.01); *A61B 18/14* (2013.01); *A61N 1/326* (2013.01); *A61N 1/3603* (2017.08); *A61N 2001/083* (2013.01)

(58) Field of Classification Search
CPC .......................... A61N 1/36031; A61N 1/0456
See application file for complete search history.

(56) References Cited

U.S. PATENT DOCUMENTS 4,408,617 A * 10/1983 Auguste ............... A61H 39/002
128/907
4,926,880 A * 5/1990 Claude .................. A61N 1/326
600/547
(Continued)

FOREIGN PATENT DOCUMENTS

JP 2006-000567 1/2006
KR 20-0389849 7/2005
(Continued)

Primary Examiner — Allen Porter
Assistant Examiner — James Moss
(74) Attorney, Agent, or Firm — Launchpad IP, Inc.; Christopher A. Wiklof; James C. Larsen

(57) ABSTRACT

A sinus treatment device and methods of operating the sinus treatment device that include an enhanced conductive tip and at least one return electrode are disclosed.

25 Claims, 16 Drawing Sheets

Related U.S. Application Data

(60) Provisional application No. 62/560,120, filed on Sep. 18, 2017, provisional application No. 62/559,792, filed on Sep. 18, 2017, provisional application No. 62/491,793, filed on Apr. 28, 2017.

(51) Int. Cl.
*A61B 18/14* (2006.01)
*A61N 1/32* (2006.01)

(56) References Cited

U.S. PATENT DOCUMENTS

| | | | | |
|---|---|---|---|---|
| 5,063,929 A | * | 11/1991 | Bartelt | A61N 1/36021 607/63 |
| 5,251,637 A | * | 10/1993 | Shalvi | A61B 5/0532 600/548 |
| 5,772,605 A | | 6/1998 | Weijand | |
| 6,109,268 A | | 8/2000 | Thapliyal et al. | |
| 6,684,107 B1 | * | 1/2004 | Binder | A61N 1/32 607/145 |
| 8,630,714 B1 | * | 1/2014 | Webb | A61N 1/0464 607/51 |
| 8,996,137 B2 | | 3/2015 | Ackermann et al. | |
| 9,002,479 B1 | * | 4/2015 | Unarce, Jr. | A61N 1/205 607/145 |
| 9,630,003 B2 | | 4/2017 | Thompson et al. | |
| 10,155,108 B2 | | 12/2018 | Ackermann et al. | |
| 10,252,048 B2 | | 4/2019 | Loudin et al. | |
| 2004/0044390 A1 | | 3/2004 | Szeles | |
| 2007/0293918 A1 | | 12/2007 | Thompson et al. | |
| 2009/0030476 A1 | | 1/2009 | Hargrove | |
| 2011/0066209 A1 | * | 3/2011 | Bodlaender | A61N 1/36021 607/46 |
| 2011/0276107 A1 | | 11/2011 | Simon et al. | |
| 2012/0316457 A1 | * | 12/2012 | Meng | A61B 5/4854 600/548 |
| 2013/0085551 A1 | * | 4/2013 | Bachinski | A61N 1/36021 607/59 |
| 2014/0296934 A1 | | 10/2014 | Gozani et al. | |
| 2014/0316485 A1 | * | 10/2014 | Ackermann | A61H 23/02 607/53 |
| 2016/0121118 A1 | * | 5/2016 | Franke | A61N 1/36046 607/135 |
| 2017/0239459 A1 | * | 8/2017 | Loudin | A61N 1/0546 |

FOREIGN PATENT DOCUMENTS

| | | |
|---|---|---|
| KR | 20-0414456 | 4/2006 |
| KR | 10-1534525 | 7/2015 |
| KR | 10-20150110935 | 10/2015 |

* cited by examiner

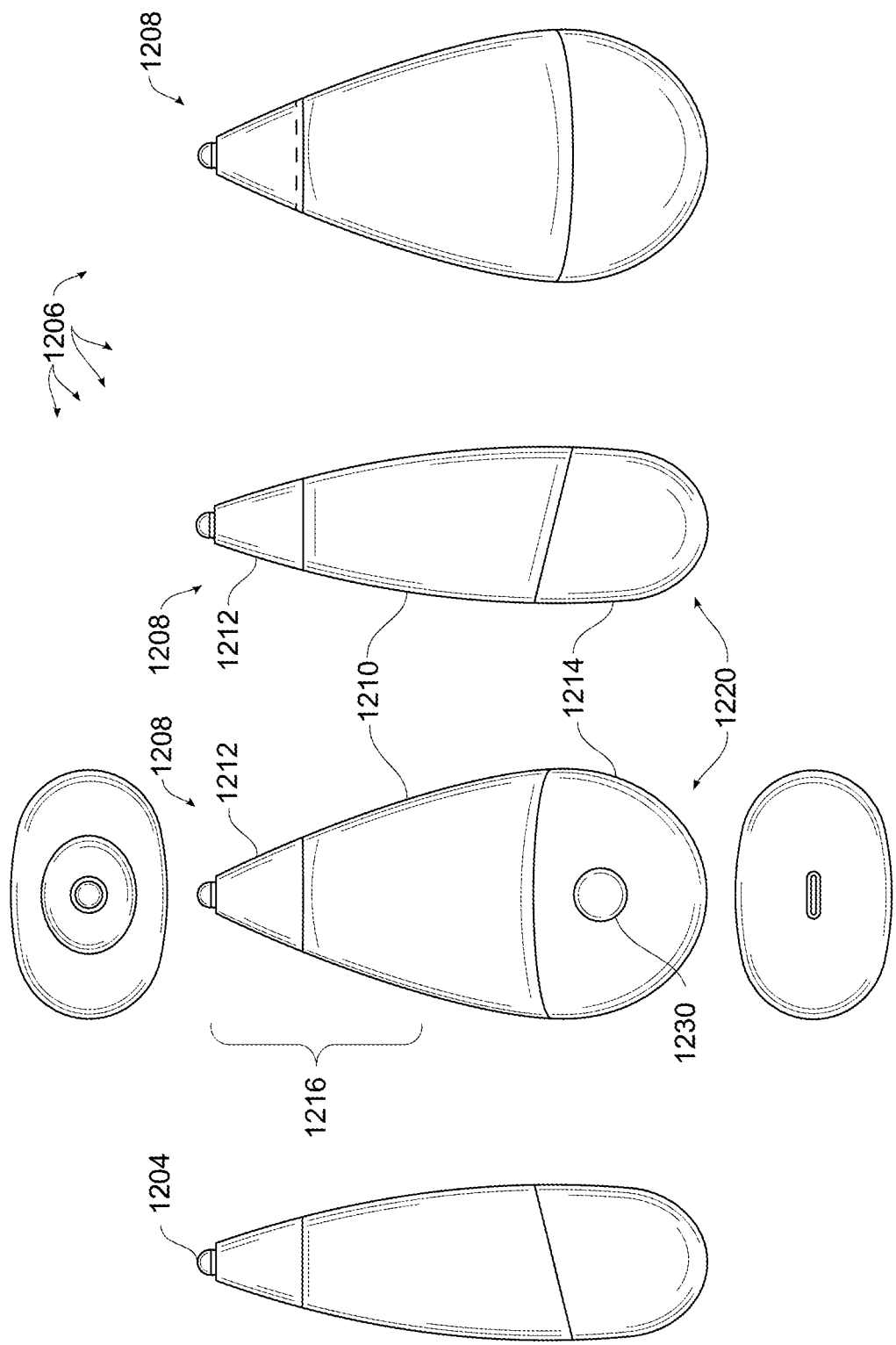

SINUS TREATMENT DEVICE WITH ENHANCED TIP

CROSS REFERENCE TO RELATED APPLICATIONS

The present application is a Continuation-in-Part Application which claims priority benefit under 35 U.S.C. § 120 (pre-AIA) of International Patent Application No. PCT/US2018/029030, entitled "SINUS TREATMENT DEVICE WITH ENHANCED TIP," filed Apr. 24, 2018. International Patent Application No. PCT/US2018/029030 claims priority benefit from U.S. Provisional Patent Application No. 62/491,793, entitled "SINUS DEVICE WITH ADAPTIVE CIRCUIT," filed Apr. 28, 2017. International Patent Application No. PCT/US2018/029030 also claims priority benefit from U.S. Provisional Patent Application No. 62/559,792, entitled "TREATMENT DEVICE INCLUDING WIRELESS INTERFACE AND USER APPLICATION," filed Sep. 18, 2017. International Patent Application No. PCT/US2018/029030 also claims priority benefit from U.S. Provisional Patent Application No. 62/560,120, entitled "ADAPTIVE TRIGGER FOR A MICROCURRENT STIMULATION DEVICE," filed Sep. 18, 2017. Each of the foregoing applications, to the extent not inconsistent with the disclosure herein, is incorporated by reference.

BACKGROUND

Every year, millions of people suffer from sinus pain, stuffiness, and drainage associated with colds, viruses, rhinosinusitis, allergies, flus, inflammation, and infection. Sinus pain can cause symptoms consistent with headaches as nasal cavities become infected, swollen, and/or inflamed. Many sinus pain patients resort to medications that can be taken orally but which also have significant side effects including drowsiness, dry mouth, nausea, and difficulty sleeping.

What is needed is an approach that can alleviate sinus symptoms without the negative effects of conventional sinus medications.

SUMMARY

According to an embodiment, a sinus treatment device includes a housing configured to be held in a hand, a return electrode operatively coupled to the housing, and a conductive tip. The sinus treatment device includes sinus treatment circuitry positioned within the housing and configured to detect sinus treatment locations on a face of a user based on an impedance between the conductive tip and the return electrode and to pass a treatment current between the conductive tip and the return electrode via the treatment location on the face of the user. The sinus treatment device includes a resilient member coupled to the conductive tip and configured to enable the conductive tip to resiliently depress toward the housing.

According to an embodiment, a sinus treatment device includes a housing configured to be held in a hand of a user, a conductive tip coupled to the housing and having a distal surface distal to the housing and a dielectric covering positioned on the distal surface and defining a covered portion of the distal surface and an exposed portion of the distal surface. The sinus treatment device includes a return electrode operatively coupled to the housing and sinus treatment circuitry positioned within the housing. The sinus treatment circuitry is configured to detect sinus treatment locations on a face of the user based on an impedance between the conductive tip and the return electrode and to pass a treatment current between the exposed portion of the distal surface of the conductive tip and the return electrode via the treatment location on the face of the user.

According to an embodiment, a method includes detecting an impedance between a conductive tip of a sinus treatment device and a return electrode of the sinus treatment device, initiating a treatment mode of the sinus treatment device when the impedance drops below a threshold by passing a sinus treatment current between the conductive tip and the return electrode, and gradually increasing a magnitude of the sinus treatment current during the treatment mode.

According to an embodiment, a method includes detecting, during a detection mode of a sinus treatment device, an impedance between a conductive tip of the sinus treatment device and a return electrode of the sinus treatment device, initiating a treatment mode of the sinus treatment device responsive to the impedance, and passing, during the treatment mode, a treatment current including a series of current spikes. The method includes gradually increasing a magnitude of the current spikes during the treatment mode until the magnitude reaches a full treatment level.

According to an embodiment, a microcurrent sinus treatment device includes a circuit configured to deliver a sequence of voltage pulses carrying a therapeutic current, and a therapeutic electrode operatively coupled to the circuit. The therapeutic electrode may be configured to apply the sequence of voltage pulses to a user's skin surface adjacent to one of a plurality of nerve nodes subjacent to the user's skin surface. The therapeutic electrode may be in electrical continuity with a therapeutic current output node of the circuit. The microcurrent sinus treatment device includes a hand holdable case configured to substantially contain active portions of the circuit. The hand holdable case includes a forward end terminating in the therapeutic electrode, and a return electrode comprising a portion of or disposed on a surface of the hand holdable case. The return electrode may be in electrical continuity with a current return node of the circuit. The hand holdable case also includes a dielectric spacer disposed between the therapeutic electrode and the return electrode, and a rearward portion of the hand holdable case terminating at an end a distance less than about four inches from the therapeutic electrode tip. The dielectric spacer and the return electrode may form a tapered surface narrowing toward the therapeutic electrode from a point of maximum girth disposed between the forward end and the rearward end of the hand holdable case.

BRIEF DESCRIPTION OF THE DRAWINGS

FIG. 12 shows several views of a microcurrent sinus treatment device, according to an embodiment.

DETAILED DESCRIPTION

Figure 1A:
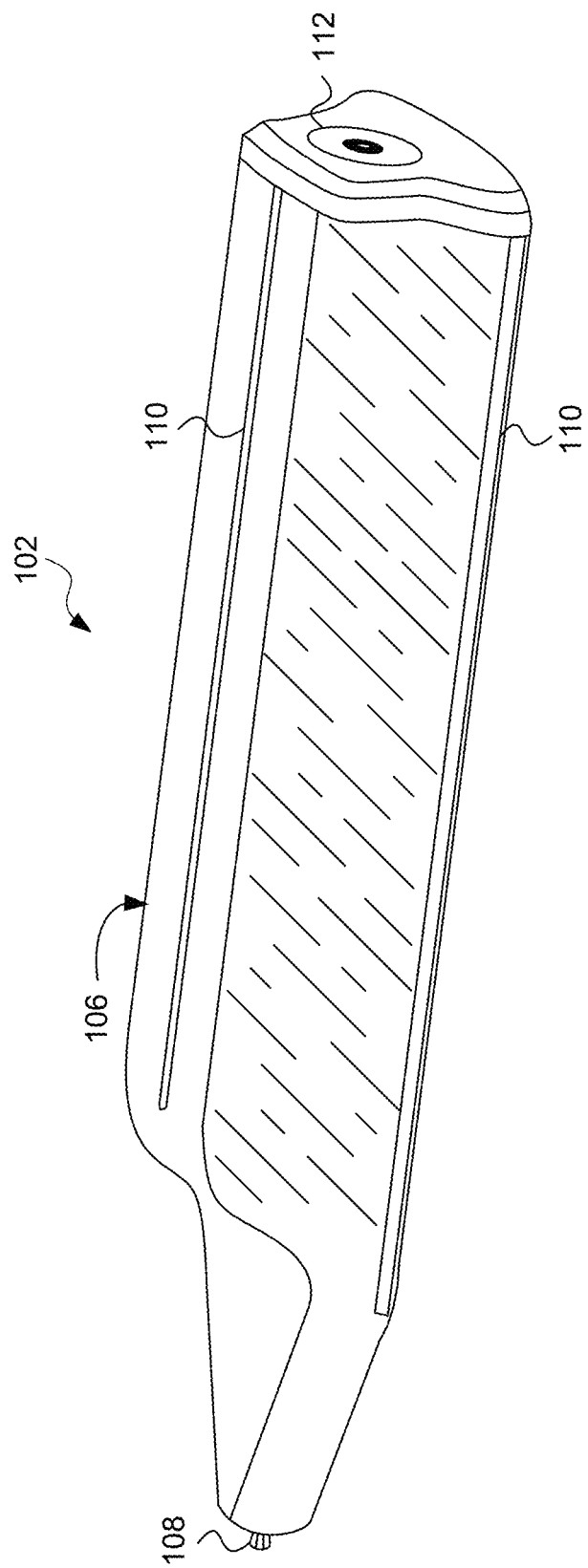
FIG. 1A is a perspective view of a handheld sinus treatment device, according to an embodiment of the disclosure.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1A is a perspective view of a handheld sinus treatment device 102, according to an embodiment. The handheld sinus treatment device 102 includes a body 106, a conductive tip 108, a return electrode 110, and a charging port 112, according to an embodiment.

According to an embodiment, the handheld sinus treatment device 102 is configured to provide sinus treatment to a user. The user holds the sinus treatment device 102 in one hand, with the hand contacting the return electrode 110, places the conductive tip 108 against the skin in the sinus region (see FIGS. 3A-3B) and glides the conductive tip 108 across the skin until the handheld sinus treatment device 102 detects a treatment location. When the handheld sinus treatment device 102 detects a treatment location, the handheld sinus treatment device 102 directs the user to hold the handheld sinus treatment device 102 still, and passes a treatment current between the conductive tip 108 and the return electrode 110. The treatment current passes through a nerve at the treatment location, thereby providing sinus relief to the user.

According to an embodiment, the body 106 is a rigid casing or housing. The body 106 has a shape that enables the user of the handheld sinus treatment device 102 to securely grip and comfortably hold the handheld sinus treatment device 102 during operation of the handheld sinus treatment device 102.

In one embodiment, the body 106 can be made from a material that is not electrically conductive. Alternatively, the body 106 can be made from a material that is electrically conductive, or can include portions that are electrically conducive, according to an embodiment. The body 106 can be made from a material that has low thermal conductivity. The body 106 is configured to protect sensitive electronic circuitry positioned within the body 106, as is described in more detail with relation to FIGS. 4-5.

According to an embodiment, the conductive tip 108 is an electrical conductor placed at a tip of the body 106. The conductive tip 108 can include a rounded shape at a point of contact with the skin of the user such that the conductive tip 108 can be placed against the skin of the user comfortably without piercing or scratching the skin. Furthermore, the shape and material of the conductive tip 108 can be selected to enable the user to comfortably glide the conductive tip 108 along the skin of the user's face adjacent to sinuses of the user. The conductive tip 108 is a treatment electrode, according to an embodiment.

According to an embodiment, the return electrode 110 includes an electrically conductive material positioned at various locations on or in the body 106. The return electrode 110 can be positioned in the body 106 at positions selected so that when the user holds the handheld sinus treatment device 102 in the user's hand, the user's hand is in contact with the return electrode 110 on one or more locations on the body 106. According to an embodiment, the return electrode 110 can include a conductive polycarbonate.

According to an embodiment, the charging port 112 is positioned at the rear of the body 106 of the handheld sinus treatment device 102. The charging port 112 is configured to receive a charging cable. When the charging cable is connected to the charging port 112, the internal battery of the handheld sinus treatment device 102 is recharged. Additionally, or alternatively, the charging port 112 can be a power supply port configured to connect to a power cable that provides power to the handheld sinus treatment device 102 while the user is using the handheld sinus treatment device 102. The charging port 112 can be a micro USB port, a USB 2.0 port, a USB 3.0 port, a USB C port, or any other kind of port that can be utilized to charge the battery of the handheld sinus treatment device 102, or to otherwise provide power to the handheld sinus treatment device 102. Additionally, or alternatively, the handheld sinus treatment device 102 can include wireless charging capability. For example, the handheld sinus treatment device 102 can include circuitry that enables inductive charging of the battery of the handheld sinus treatment device 102 such that when the handheld sinus treatment device 102 is positioned on a charging dock, the battery is recharged by inductive charging.

Figure 1B:
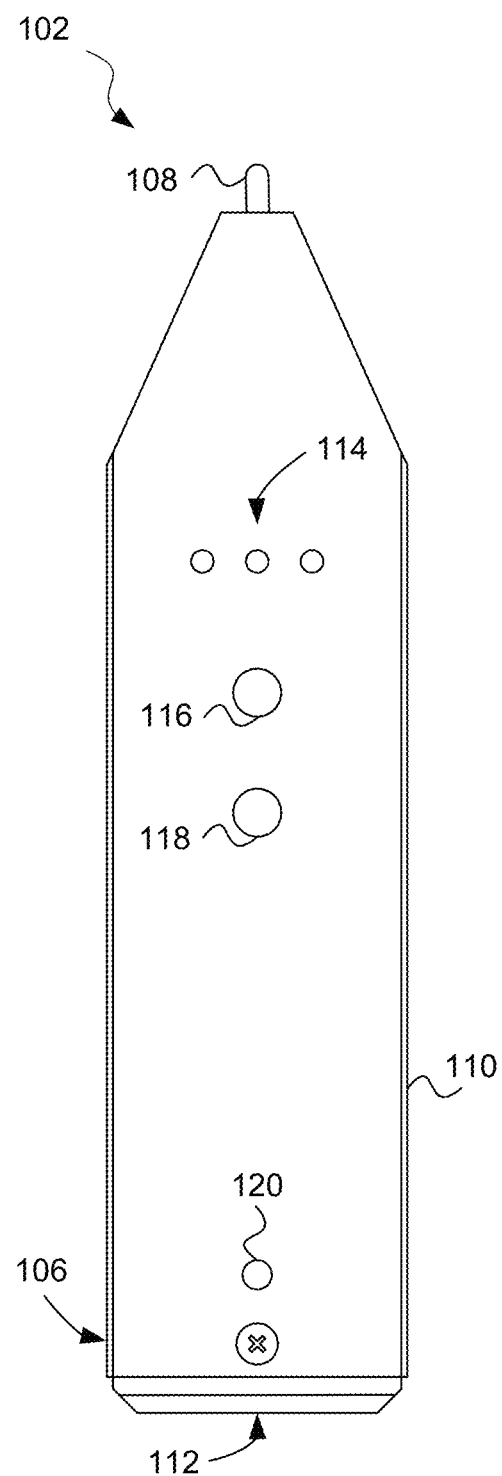
FIG. 1B is a top view of the handheld sinus treatment device of FIG. 1A, according to an embodiment of the disclosure.

FIG. 1B is a top view of a handheld sinus treatment device 102, according to an embodiment. The top view of the handheld sinus treatment device 102 illustrates the body 106, the conductive tip 108, the return electrode 110, the charging port 112, indicators 114, a sensitivity setting button 116, a power button 118, and a low battery indicator 120.

According to an embodiment, the indicators 114 can provide an indication of the sensitivity level of the handheld sinus treatment device 102. The sensitivity level corresponds to a sensitivity setting for detecting treatment areas adjacent to the sinuses of the user. The indicators 114 can include multiple LED indicators. The handheld sinus treatment device 102 can illuminate a number of the sensitivity level indicator LEDs 114 to indicate a sensitivity level of the handheld sinus treatment device 102 during a detection mode. A greater number of illuminated indicator LEDs 114 can correspond to a higher sensitivity level. A lesser number of illuminated indicator LEDs 114 can correspond to a lower sensitivity level. Alternatively, other schemes for illuminating LEDs to indicate a sensitivity level of the detection mode of the handheld sinus treatment device 102 can be utilized. Additionally, the indicators 114 can include indicators other than LEDs. For example, the indicators 114 can include various types of lights, a display panel, or other types of indicators capable of providing an indication of the sensitivity level of the handheld sinus treatment device 102 during a detection mode of the handheld sinus treatment device 102. According to an embodiment, the indicators 114 can also signal that a treatment location has been identified, that treatment stimulation is currently being provided, that another treatment location should be identified, or other parameters of operation of the handheld sinus treatment device 102.

According to an embodiment, the sensitivity setting button 116 is configured to enable the user to adjust the sensitivity of the handheld sinus treatment device 102 during a detection mode. The user can manipulate the sensitivity setting button 116 in order to increase or decrease the sensitivity of the handheld sinus treatment device 102. For example, the user can press the sensitivity setting button 116 to adjust the sensitivity of the handheld sinus treatment device 102. Additionally, or alternatively, the user can toggle or slide the sensitivity setting button 116 in order to adjust the sensitivity of the handheld sinus treatment device 102. Additionally, or alternatively, the sensitivity setting button 116 can include multiple buttons for adjusting the sensitivity of the handheld sinus treatment device 102. A first button can be used to decrease the sensitivity. A second button can be used to increase the sensitivity. Additionally, or alternatively, the handheld sinus treatment device 102 can include a touchscreen that enables the user to adjust the sensitivity of the handheld sinus treatment device 102.

According to an embodiment, the power button 118 is configured to enable the user to turn the handheld sinus treatment device 102 on or off. For example, if the handheld sinus treatment device 102 is currently off, then the user can turn the handheld sinus treatment device 102 on by pressing, toggling, sliding, or otherwise manipulating, the power button 118. If the handheld sinus treatment device 102 is currently on, then the user can turn the handheld sinus treatment device 102 off by pressing, toggling, sliding, or otherwise manipulating the power button 118. Alternatively, the sensitivity setting button 116 and the power button 118 can be implemented in a single button or switch that can adjust the sensitivity or turn the handheld sinus treatment device 102 on or off based on a length of a button press, a number of button presses, or other types of manipulations of the single button.

According to an embodiment, the low battery indicator 120 can provide an indication of a state of charge of the battery of the handheld sinus treatment device 102. The low battery indicator 120 can include one or more LEDs. When the battery of the handheld sinus treatment device 102 is low, one or more LEDs of the low battery indicator 120 can become illuminated. If the low battery indicator 120 includes a single LED, then the single LED can become illuminated when the battery is nearing depletion. Conversely, the single LED may not be illuminated when the battery is not nearing depletion. Alternatively, when the battery is nearing depletion, a first LED of a first color can be illuminated to indicate that the battery is nearing depletion. If the battery is not nearing depletion, then a second LED of a second color can be illuminated indicating that the battery is not nearing depletion.

According to an embodiment, portions of the return electrode 110 are positioned on the sides of the body 106 of the handheld sinus treatment device 102. When the user grips the handheld sinus treatment device 102 such that a thumb of the user is in a position to manipulate the sensitivity setting button 116 and the power button 118, the palm and/or fingers of the hand of the user will be in contact with the portion of the return electrode 110 positioned on the sides of the body 106 of the handheld sinus treatment device 102.

Figure 1C:
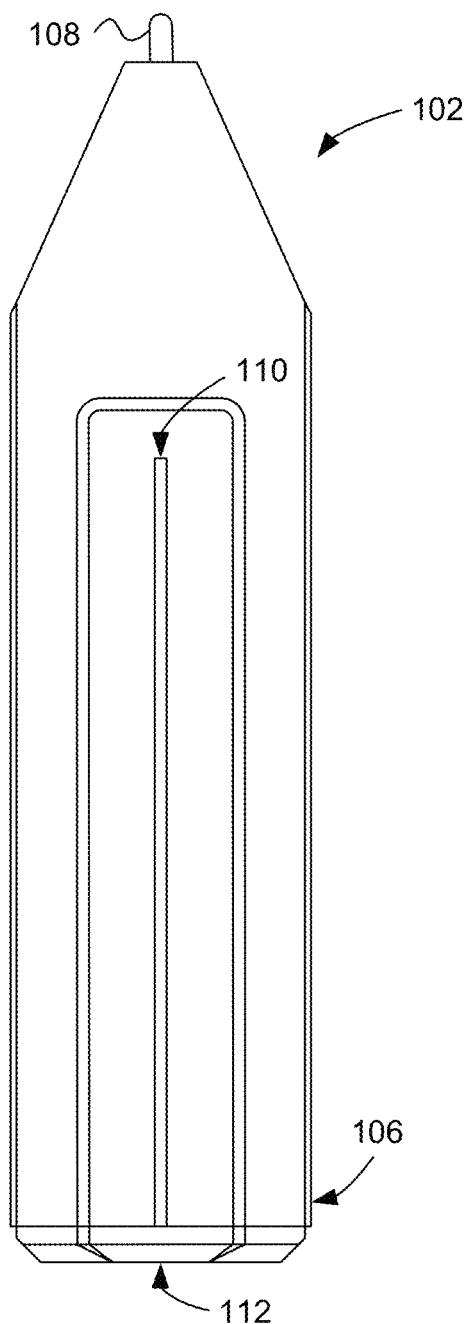
FIG. 1C is a bottom view of the handheld sinus treatment device of FIG. 1A, according to an embodiment of the disclosure.

FIG. 1C is a bottom view of the handheld sinus treatment device 102 of FIG. 1B, according to an embodiment. The bottom view of the handheld sinus treatment device 102 illustrates a portion of the return electrode 110 positioned on the bottom portion of the body 106 of the handheld sinus treatment device 102. The positioning of a portion of the return electrode 110 on the bottom of the body 106 of the handheld sinus treatment device 102 further ensures that when the user holds the handheld sinus treatment device 102 in the user's hand, the user's hand will be in contact with the return electrode 110.

Figure 2:
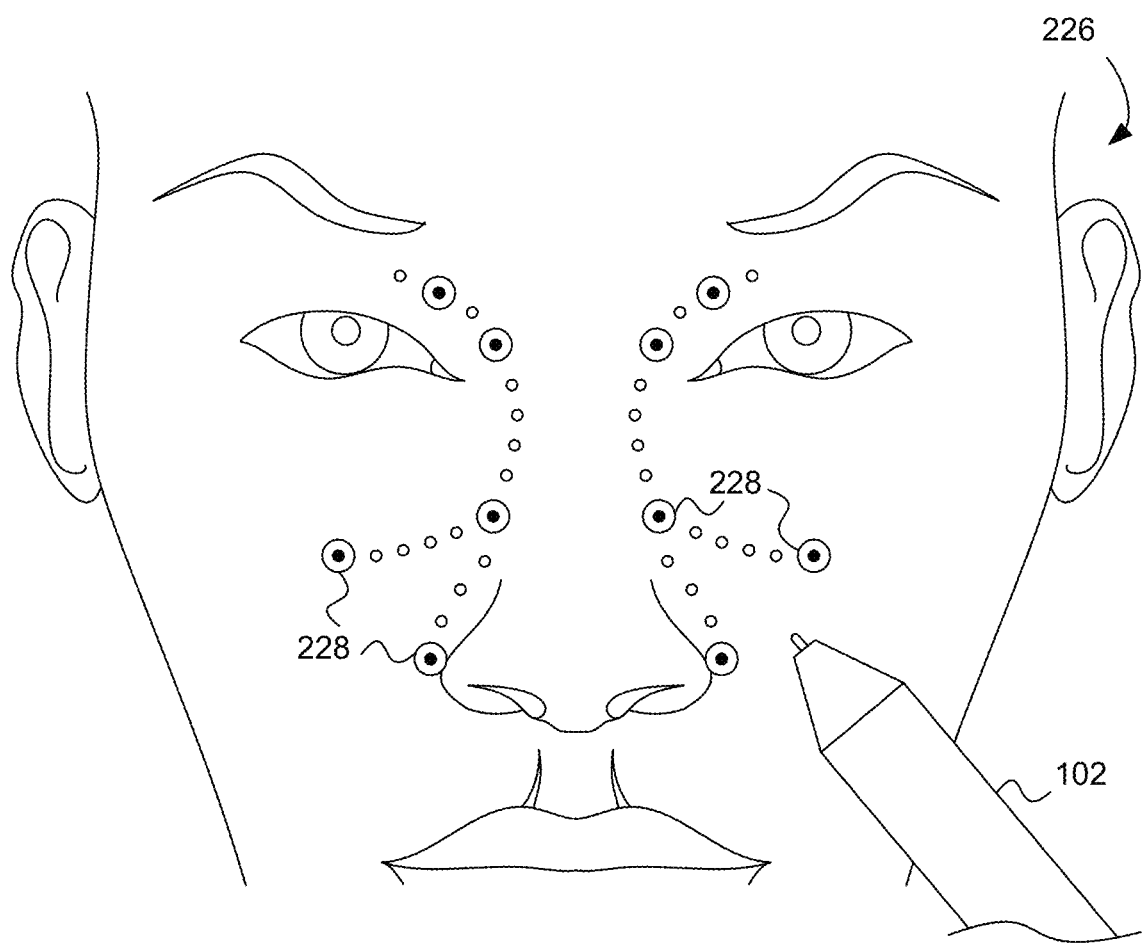
FIG. 2 is an illustration of a handheld sinus treatment device providing sinus relief treatment to highlighted treatment areas adjacent to the sinuses of a user, according to an embodiment of the disclosure.

FIG. 2 is an illustration of a face 226 of a user of the handheld sinus treatment device 102 highlighting treatment areas 228. According to an embodiment, the treatment areas 228 correspond to nerve nodes. The nerve nodes are treatment locations 228 at which sinus nerves pass through the skull.

According to an embodiment, the user uses the handheld sinus treatment device 102 by holding the body 106 in one hand such that the user's hand is in contact with portions of the return electrode 110. The user then places the conductive tip 108 on the skin adjacent to the sinuses and glides the conductive tip 108 over the skin during a detection mode of the handheld sinus treatment device 102. In the detection mode, the handheld sinus treatment device 102 detects the treatment location 228, corresponding to the location of a nerve node beneath the skin. When the handheld sinus treatment device 102 detects the treatment location 228 of a nerve node beneath the skin, the handheld sinus treatment device 102 can enter a treatment mode.

In one embodiment, the handheld sinus treatment device 102 detects treatment locations 228 by detecting an impedance between the conductive tip 108 and the return electrode 110. Treatment locations 228 are characterized by a lower impedance than surrounding areas due to enhanced conductivity of nerves.

According to an embodiment, in the treatment mode, the handheld sinus treatment device 102 provides treatment stimulation to the treatment location 228, corresponding to the nerve that is located during the detection mode. The handheld sinus treatment device 102 can provide treatment stimulation to the treatment location 228 by providing electrical stimulation to the treatment location 228. The electrical stimulation can affect the nerve node in such a way that the user experiences relief from troubling sinus symptoms such as pain, congestion, inflammation, or other unpleasant symptoms.

According to an embodiment, the handheld sinus treatment device 102 is a transcutaneous electrical nerve stimulation (TENS) device. The handheld sinus treatment device 102 applies electrical treatment stimulation in the form of a treatment current having selected characteristics. The treatment current can have an average magnitude that is multiple orders of magnitude lower than common TENS devices. According to an embodiment, the treatment current does not have a DC component, but is characterized by current spikes of alternating polarity. According to an embodiment, the treatment stimulation is provided at each treatment location 228 for a period of time between 2-10 seconds.

According to an embodiment, the handheld sinus treatment device 102 applies the treatment current by applying a stimulation voltage between the conductive tip 108 and the return electrode 110.

According to an embodiment, the conductive tip 108 is the active electrode of a monopolar design. The housing/body 106 of the handheld sinus treatment device 102 may serve as the return electrode 110 when return electrodes 110 are integrated into the body 106. A user's hand holding the handheld sinus treatment device 102 completes the electrical path from the conductive tip 108 to the return electrode(s) 110 in that currents may travel from the conductive tip 108, through the nasal area of the user and down to the hand of the user that is contacting the return electrode(s) 110, in an embodiment. These currents may be referred to as "treatment currents" in this disclosure.

According to an embodiment, in the detection mode, the user presses the conductive tip 108 to the skin and the handheld sinus treatment device 102 initiates a low-frequency circuit that is maintained at a constant current. The handheld sinus treatment device 102 may use the current to calculate the impedance in the path between the tissue at the conductive tip 108 and the hand in contact with the handheld sinus treatment device 102. The handheld sinus treatment device 102 remains in the detection mode until the detection current indicates that the impedance is below a threshold impedance. The position of the conductive tip 108 when the impedance is below the threshold impedance corresponds to a treatment area 228. The treatment area 228 corresponds to a nerve node area. When the handheld sinus treatment device 102 identifies a treatment area 228 based on the calculated impedance, the handheld sinus treatment device 102 can enter the treatment mode and can deliver treatment stimulation to the identified treatment area 228.

According to an embodiment, the handheld sinus treatment device 102 can indicate to the user that the handheld sinus treatment device 102 is in the treatment mode and that the user should hold the conductive tip 108 at the treatment location 228 for a selected period of time. According to an embodiment, the handheld sinus treatment device 102 can indicate the transition between the detection mode and the treatment mode by the indicators 114. The indicators 114 can include one or more LEDs that can provide an illumination scheme that indicates whether the handheld sinus treatment device 102 is in the detection mode or the treatment mode. According to an embodiment, the handheld sinus treatment device 102 can indicate that the handheld sinus treatment device 102 is in the treatment mode via haptic feedback (vibration). According to an embodiment, the handheld sinus treatment device 102 can indicate whether the handheld sinus treatment device 102 is in the detection mode, the treatment mode, or transitioning between the detection and the treatment modes by a combination of haptic feedback and the LED indicators 114. According to an embodiment, when the handheld sinus treatment device 102 enters the treatment mode as indicated by one or more of the LED indicators 114 and haptic feedback, the user holds the handheld sinus treatment device 102 in place until the treatment period has passed as indicated by cessation of haptic feedback and the LED indicators 114 (approximately 8 seconds in one example).

According to an embodiment, once the treatment period ends, the handheld sinus treatment device 102 resets to detection mode. The user then may continue to glide the handheld sinus treatment device 102 along the indicated path until reaching the next treatment area 228 as identified based on impedance calculations. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the output current, in one embodiment.

In one embodiment of a treatment circuit of the disclosed handheld sinus treatment device 102, the constant current stimulation output is approximately 1 Hz-1000 Hz, bi-phasic, no DC component signal with an average current less than 1000 μA over a resistive load of 10K-100KΩ. The signal is presented to the user by means of the conductive tip 108, in one embodiment. According to an embodiment, the spring-loaded conductive tip 108 activates the circuit and gently ramps the current to provide maximal comfort to the user.

According to an embodiment, constant current stimulation circuit output is directed to the conductive tip 108 and returned to the circuit by way of the return electrode 110 (metallized portions of the enclosure). When the circuit is completed by the user pressing the device conductive tip 108 to the face 226, a microcontroller monitors the resulting treatment current and controls the stimulation voltage (across the conductive tip 108 and the return electrode 110) to maintain the desired current, in one embodiment. The impedance of the circuit is then calculated and monitored by the microcontroller. In the event that the impedance falls below a specified threshold, which is indicative of a treatment location 228, the microcontroller presents a treatment prompt through a user interface (UI), in one embodiment. According to an embodiment, the user is instructed to maintain the conductive tip 108 location until the treatment prompt has timed out. After treatment time out, the user is instructed to slowly move the conductive tip 108 to the next detected treatment location 228, in one embodiment.

According to an embodiment, the sensitivity level setting determines the impedance threshold at which the handheld sinus treatment device 102 will signal the user to detection of a treatment location 228. The treatment sensitivity threshold may be increased to compensate for higher impedance associated with dry skin or the presence of makeup, in one embodiment. Upon detection of a treatment location 228, the haptic motor starts to vibrate and the sensitivity level indicator LEDs 114 flash for a pre-programmed period of time, in one embodiment. If the calculated impedance increases above the threshold (conductive tip 108 removed from the face 226 or moved to a higher impedance location on the face 226), the treatment session may be terminated.

In one embodiment, the handheld sinus treatment device 102 is used as a handheld microcurrent TENS device used for the temporary relief of sinus pain. The handheld sinus treatment device 102 uses an average treatment current that is several orders of magnitude smaller than that of previously cleared TENS devices, in one embodiment. In one embodiment, the handheld sinus treatment device 102 is a sinus treatment device designed to provide transcutaneous nerve stimulation to the regional areas associated with the sinuses, and current levels are attuned to those appropriate for facial treatments, as seen in predicate facial toners.

The sinus treatment device 102 is held in the hand, with the conductive tip 108 of the handheld sinus treatment device 102 applied to the skin on the outside of the sinus passages. In one embodiment, the conductive tip 108 is the active electrode of a monopolar design. The housing/body 106 of the handheld sinus treatment device 102 may serve as the return electrode 110 when return electrodes 110 are integrated into the body 106. A user's hand holding the sinus treatment device 102 completes the electrical path from the conductive tip 108 to the return electrode(s) 110 in that treatment currents may travel between the conductive tip 108 and the return electrode 110 through the nasal area. The treatment current can be passed in either direction between the conductive tip 108 and the return electrode 110 through the body of the user, according to an embodiment. The treatment current can alternate directions during the treatment mode, according to an embodiment.

In one embodiment, when the user turns the handheld sinus treatment device 102 "ON" and presses the conductive tip 108 to the skin, the handheld sinus treatment device 102 initiates a low-frequency circuit that is maintained at a constant detection current. The handheld sinus treatment device 102 may use the detection current to calculate the impedance in the path between the tissue at the conductive tip 108 and the hand in contact with the handheld sinus treatment device 102. In one embodiment, if the calculated impedance is above an impedance threshold, the handheld sinus treatment device 102 is in "detection" mode. Conversely, in one embodiment, when the impedance falls below the impedance threshold, the handheld sinus treatment device 102 enters a "treatment" mode. In one embodiment, in the treatment mode the treatment current is has a greater magnitude than the current used in the detection mode.

In one embodiment, the user is instructed to glide the conductive tip 108 of the handheld sinus treatment device 102 along the skin, in accordance with an embodiment of the disclosure. The switch (transition) from detection mode to the treatment mode is signaled to the user via haptic (vibration) feedback and blinking of the indicator LEDs 114, in one embodiment. The user then holds the handheld sinus treatment device 102 in place until the treatment period has passed as indicated by cessation of haptic and LED indicators 114 (approximately 8 seconds in one example), in one embodiment.

In one embodiment, once the treatment period ends, the handheld sinus treatment device 102 resets to detection mode. The user then may continue to glide the handheld sinus treatment device 102 along the indicated path until reaching the next low-impedance area. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the treatment current, in one embodiment.

In one embodiment, the sensitivity setting button 116 may allow a user to toggle through different sensitivity levels that may be indicated by the example illustrated three indicator LEDs 114, in FIGS. 1A-1C. In one embodiment, an overcoat/insulator may cover the body 106 of the handheld sinus treatment device 102 except for where the return electrode 110 provides an electrical path.

In one embodiment, the conductive tip 108 includes an elastomeric material intended to minimize point pressure against the face 226 of the user. Various elastomers including silicone, fluorine-substituted silicones, natural rubber, vulcanized rubber, latex, latex derivatives, etc. may be used alone or in combination to form a support structure of the conductive tip 108. In another embodiment, a non-elastomeric dielectric material such as a polymer, polymer combination, or glass may be used alone or in combination to form the support structure of the active electrode. The support structure may be formed to have a relatively low thermal conductivity and/or may have a smooth radius to reduce point pressure against the skin of the user. Various conductive fibers or particles such as gold, silver, stainless steel, carbon fiber, carbon nanotubes, and/or alternating bond length (electron-conjugated) polymers are contemplated as current carriers supported by a dielectric support structure.

In one embodiment, the handheld sinus treatment device 102 includes a spring-loaded conductive tip 108 and the conductive tip 108 is a small surface area metalized feature (tip) of the enclosure that is applied to the treatment regions of the face 226. In one embodiment, a microswitch initiates the therapy circuit when the conductive tip 108 is depressed. The handheld sinus treatment device 102 may include a microprocessor, microcontroller, a battery, and a transformer/voltage step-up circuit. In one embodiment, the return electrode 110 is a large surface area metalized region of the enclosure that is in contact with the user's hand.

In one embodiment, the user interface of the handheld sinus treatment device 102 includes an LED treatment indicator 114 (e.g., LEDs 114), a sensitivity level adjustment button 116, and a haptic feedback circuit. The LED sensitivity level indicates selected sensitivity levels in addition to low battery and charge status, an on/off button with integrated LED(s) 118 to indicate "on" or "off" state, and a haptic feedback circuit.

In one embodiment, the handheld sinus treatment device 102 includes an overcoat that is electrically insulated. The overcoat may cover a portion of the metalized return electrode 110 so long as a portion (e.g., 10%) of the return electrode 110 is exposed. In one embodiment, the handheld sinus treatment device 102 includes a battery charging port 112 and circuit to charge an internal battery.

As described above, the handheld sinus treatment device 102 may be used as a TENS device that applies microamp electrical stimulation to facial nerves around the sinuses which are the regions around the nose and the supraorbital region of the eye. The locations of the low impedance points in the facial skin correlate strongly with various foramina (holes) through which major nerve fibers pass from the sinus passages, through the skull, to areas near the skin.

Figure 3B:
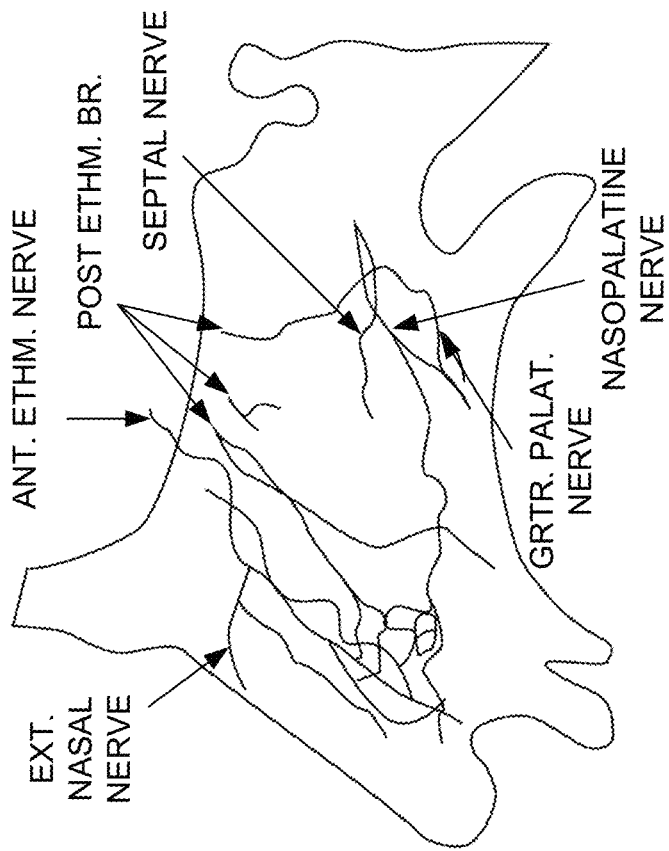
FIGS. 3A and 3B illustrate nasal pathways and associated nerves that a sinus treatment device may be applied to, according to an embodiment of the disclosure.
Figure 3A:
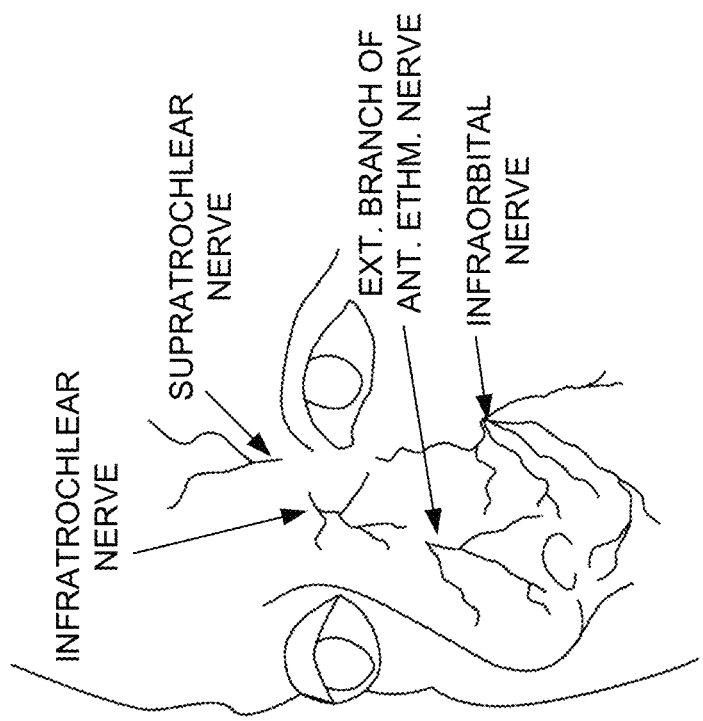

FIGS. 3A and 3B illustrate nasal pathways and associated nerves that the handheld sinus treatment device 102 may be applied to by a user to facilitate treatment/therapy.

In one embodiment of a treatment circuit of the disclosed handheld sinus treatment device 102, the constant current stimulation output is approximately 1 Hz-1000 Hz, bi-phasic, no DC component signal with an average current –less than 1000 μA over a resistive load of 10K-100KΩ. The signal is presented to the user by means of the monopolar electrode, in one embodiment. In one embodiment, the spring-loaded conductive tip 108 activates the circuit and gently ramps the current to provide maximal comfort to the user.

In one embodiment, constant current stimulation circuit output is directed to the conductive tip 108 (the device tip 108) and returned to the circuit by way of the return electrode 110 (metallized portions of the enclosure). When the circuit is completed by the user pressing the device conductive tip 108 to the face 226, a microcontroller monitors the resulting treatment current and controls the stimulation voltage (across the conductive tip 108 and return electrode 110) to maintain the desired current, in one embodiment. The impedance of the circuit is then calculated and monitored by the microcontroller. In the event that the impedance falls below a specified threshold, which is indicative of a treatment location 228, the microcontroller presents a treatment prompt through the user interface (UI), in one embodiment. In one embodiment, the user is instructed to maintain the conductive tip 108 location until the treatment prompt has timed out. After treatment time out, the user is instructed to slowly move the conductive tip 108 to the next detected treatment location 228, in one embodiment.

In one embodiment, the sensitivity level setting determines the impedance threshold at which the handheld sinus treatment device 102 will signal the user to detection of a treatment location 228. The treatment sensitivity threshold may be increased to compensate for higher impedance associated with dry skin or the presence of makeup, in one embodiment. Upon detection of a treatment location 228, the haptic motor starts to vibrate and the sensitivity level indicator LEDs 116 flash for a pre-programmed period of time, in one embodiment. If the calculated impedance increases above the threshold (conductive tip 108 removed from the face 226 or moved to a higher impedance location on the face 226), the treatment session may be terminated.

Figure 4:
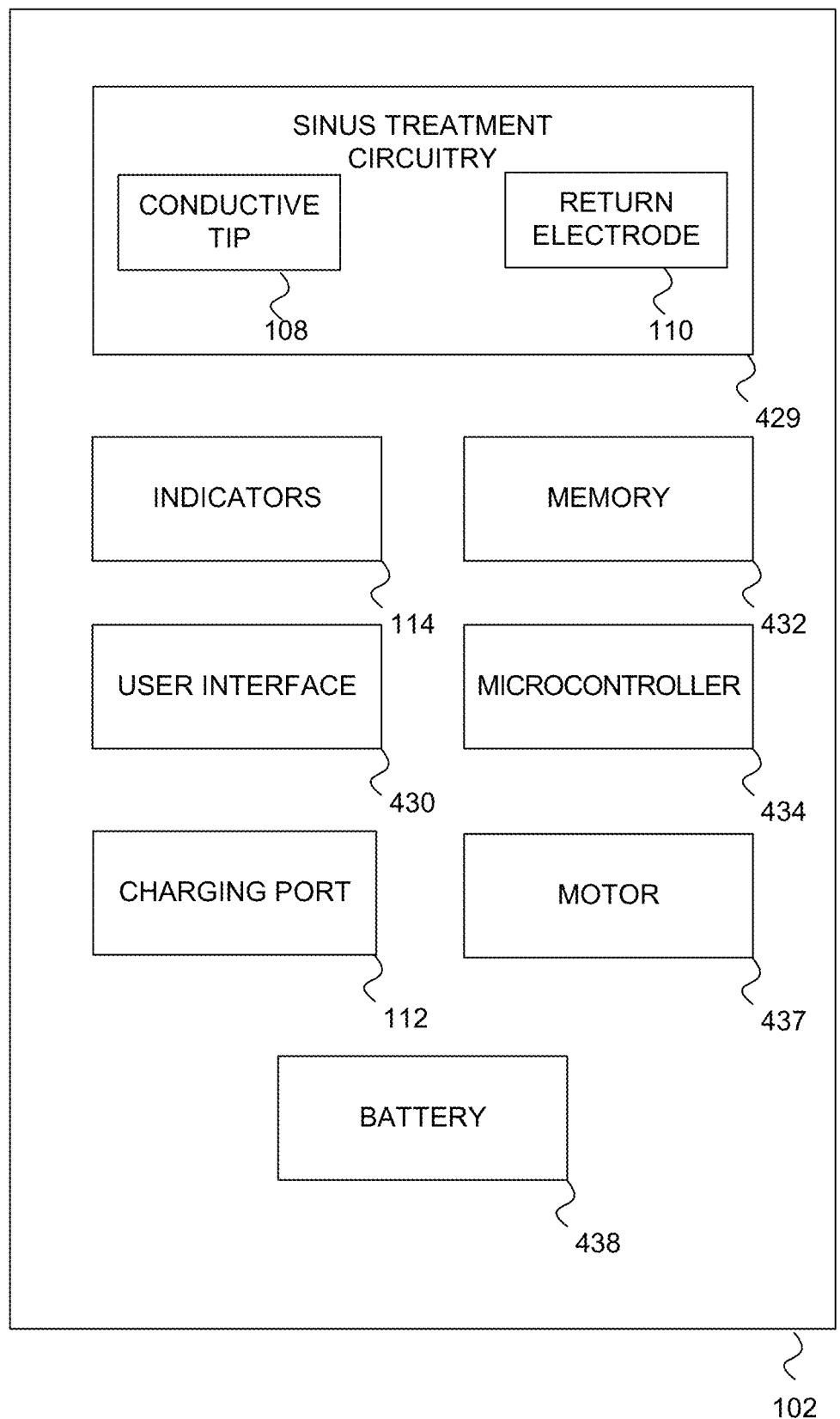
FIG. 4 is a block diagram of a sinus treatment device, according to an embodiment of the disclosure.

FIG. 4 is a block diagram of the handheld sinus treatment device 102, according to an embodiment. The handheld sinus treatment device 102 includes a sinus treatment circuitry (or current output circuit) 429, the charging port 112, the indicators 114, a user interface 430, a memory 432, a microcontroller 434, a motor 437, and a battery 438. The current output circuit 429 includes the conductive tip 108 and the return electrode 110. The handheld sinus treatment device 102 utilizes these components to provide effective sinus relief treatments to the user.

According to an embodiment, the conductive tip 108 and the return electrode 110 cooperate together to provide both detection currents and treatment stimulation. Detection and treatment currents are passed between the conductive tip 108 and the return electrode 110 through the body of the user. In particular, the conductive tip 108 is positioned in contact with the user's skin to the sinus areas of the user. The return electrode 110 is in contact with the user's hand as the user holds the handheld sinus treatment device 102. The detection and treatment currents pass between the conductive tip 108 and the return electrode 110 via the hand, body, and facial skin of the user.

According to an embodiment, the indicators 114 provide indications to the user as to the current mode of operation of the handheld sinus treatment device 102. The indicators 114 can include one or more LEDs that can be illuminated in selected ways to indicate whether the handheld sinus treatment device 102 is powered on, whether the handheld sinus treatment device 102 is in a treatment mode, whether the handheld sinus treatment device 102 is in a detection mode, whether the handheld sinus treatment device 102 awaits user input, or indications of other types of functionality of the handheld sinus treatment device 102. According to an embodiment, the indicators 114 can include a display capable of outputting text or images to indicate to the user the various functions of the handheld sinus treatment device 102.

According to an embodiment, the user interface 430 includes various components that enable the user to control functionality of the handheld sinus treatment device 102. The user interface 430 can include the power on-off button 118, the sensitivity setting button 116, or other kinds of buttons, switches, touchscreens, or input controls that enable the user to control functionality of the handheld sinus treatment device 102. The user can manipulate the user interface 430 in order to control the functionality of the handheld sinus treatment device 102.

According to an embodiment, the memory 432 stores data related to the functionality of the handheld sinus treatment device 102. The memory 432 can include software instructions by which the various functionalities of the handheld sinus treatment device 102 can be implemented. The memory 432 can include reference impedance values and/or threshold impedance values. The reference and threshold impedance values can be utilized in the detection mode of the handheld sinus treatment device 102. The memory 432 can include data indicating previously detected treatment locations 228. The memory 432 can include other settings such as treatment lengths, treatment stimulation strengths, frequencies of treatments, or other settings including default settings and user selected settings for operation of the handheld sinus treatment device 102. The memory 432 can include one or more of EEPROMs, flash memory, ROMs, SRAM, DRAM, or other kinds of computer readable media capable of storing instructions that can be executed by the microcontroller 434.

According to an embodiment, the motor 437 enables the handheld sinus treatment device 102 to provide haptic feedback to the user. For example, during a treatment mode in which the handheld sinus treatment device 102 provides stimulation treatment to a treatment area 228, the motor 437 can cause the handheld sinus treatment device 102 to vibrate mildly to indicate to the user that the handheld sinus treatment device 102 is in the treatment mode. The motor 437 can cease the vibration to indicate that the handheld sinus treatment device 102 is no longer in the treatment mode. The motor 437 can generate vibrations to provide a variety of types of indications to the user of the handheld sinus treatment device 102.

According to an embodiment, the battery 438 provides power to the handheld sinus treatment device 102. The battery 438 can include a rechargeable battery 438 that enables the user to recharge the battery 438 after the battery 438 has become depleted through use. The battery 438 can be a lithium-ion battery, a NiCad battery, a carbon zinc battery, an alkaline battery, a nickel metal hydride battery, or other types of batteries.

According to an embodiment, the charging port 112 enables the user to recharge the battery 438. For example, the charging port 112 can be configured to receive a charging cable that connects the charging port 112 to a power source. The charging port 112 can include a micro USB port, a USB 2.0 port, a USB 3.0 port, a USB C port, or other types of charging ports. According to an embodiment, the charging port 112 enables charging and data transmission. When a charging cable is plugged into the charging port 112, the battery 438 can be charged and data can be received or transmitted over the charging cable via the charging port 112. According to an embodiment, the handheld sinus treatment device 102 can operate while a charging cable is attached to the charging port 112. Thus, if the battery 438 is depleted, the user can attach a charging cable to the charging port 112 and can operate the handheld sinus treatment device 102 from power received via the charging port 112.

According to an embodiment, the microcontroller 434 controls the functionality of the other components of the handheld sinus treatment device 102. The microcontroller 434 is communicatively coupled to the conductive tip 108, the return electrode 110, the indicators 114, the memory 432, the user interface 430, and the charging port 112.

According to an embodiment, the microcontroller 434 executes the software instructions stored in the memory 432 to implement the various modes of functionalities of the handheld sinus treatment device 102. The microcontroller 434 causes the conductive tip 108 and the return electrode 110 to pass the detection currents in the detection mode, and to pass the treatment currents in the treatment mode. The microcontroller 434 controls the indicators 114 to indicate the various modes of functionalities of the handheld sinus treatment device 102. The microcontroller 434 communicates with the user interface 430 to enable the user to select various modes of operation of the handheld sinus treatment device 102.

Figure 5:
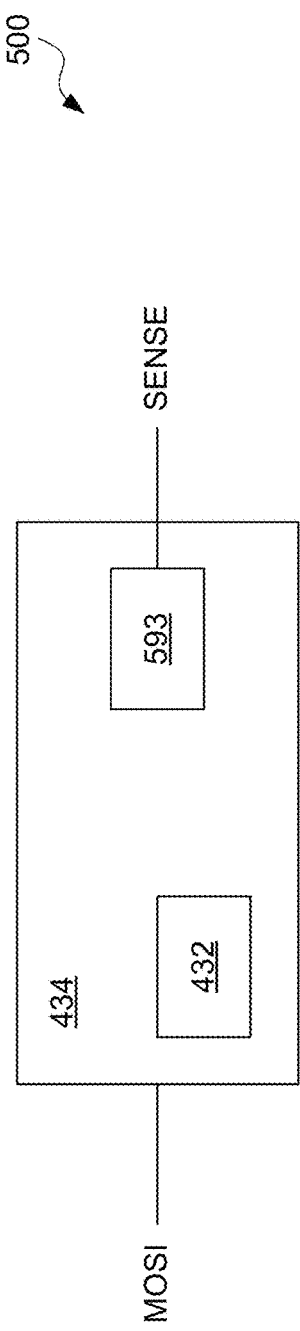
FIG. 5 illustrates an example adaptive output circuit for use with a sinus treatment device, according to an embodiment of the disclosure.
Figure 5:
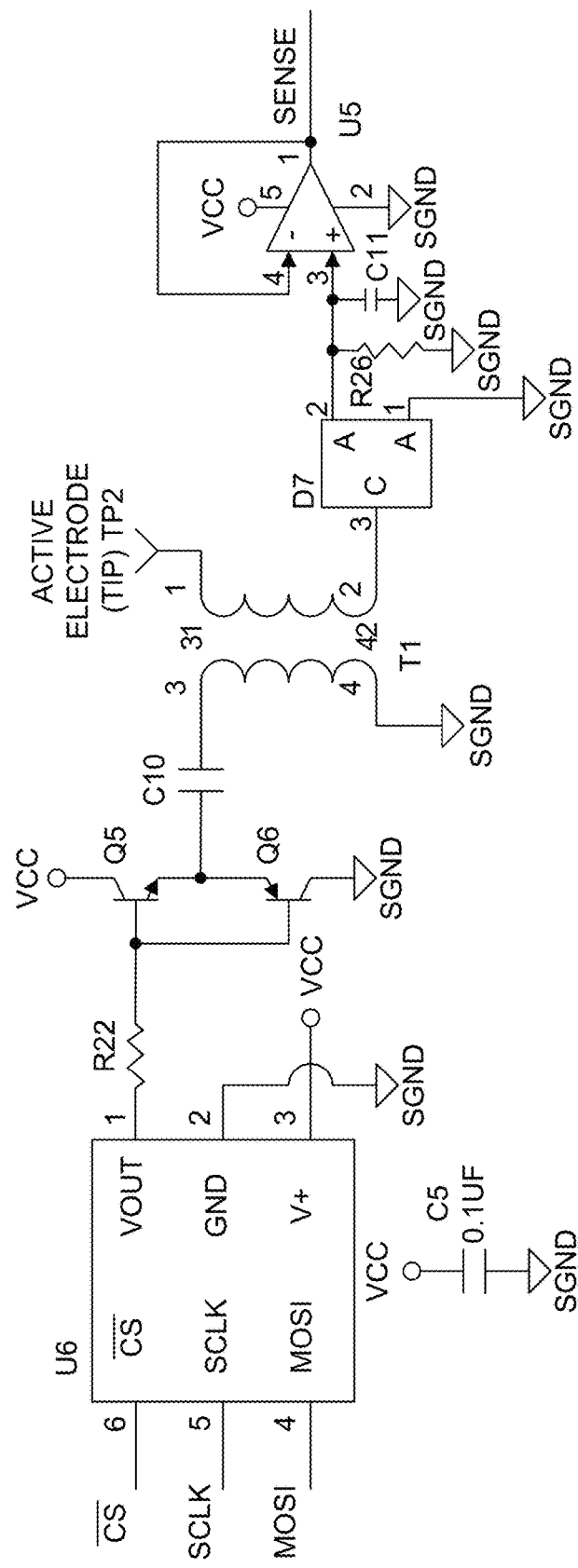

FIG. 5 illustrates an example sinus treatment circuitry 500 for use with the handheld sinus treatment device 102, according to an embodiment of the disclosure. The sinus treatment circuitry 500 is positioned within the housing/body 106, according to one embodiment. The sinus treatment circuitry 500 includes a microcontroller 434 including a memory 432 and an analog-to-digital converter (ADC) 593. In the illustrated embodiment of FIG. 5, the sinus treatment circuitry 500 also includes a stimulation driver stage and a peak detector.

In one embodiment, the stimulation driver stage is coupled to apply a stimulation voltage between the conductive tip (active electrode TP2) and the return electrode 110 (not illustrated in FIG. 5). In the illustrated embodiment, the stimulation driver stage includes a digital-to-analog converter (DAC), an amplifier, a transformer, and a capacitor. In one embodiment, the DAC (U6) is coupled to generate an analog voltage (pin 1 of U6, VOUT) in response to a digital instruction from the microcontroller 434 received via the MOSI (Master Out Slave In) communication channel of pin 4 of U6.

In the illustrated embodiment, the amplifier includes transistors Q5 and Q6 and is coupled to generate an amplified analog voltage (emitter node of Q5) in response to receiving the analog voltage from the DAC (U6).

In the illustrated embodiment, the transformer T1 includes a primary side (nodes 3 and 4) and a secondary side (nodes 1 and 2). The conductive tip (active electrode TP2) is coupled to node 1 of the secondary side of the transformer T1, in the illustrated embodiment.

In the illustrated embodiment, capacitor C10 is coupled between the amplifier and a primary side of the transformer T1 to block the DC (direct current) portions of the amplified analog signal.

In one embodiment, the peak detector includes a diode element, a buffer circuit, and a sample and hold circuit. In the illustrated embodiment, the diode element is D7. In one embodiment, the buffer circuit is coupled to output a peak treatment current signal. In one embodiment, the peak detector is coupled to generate a peak treatment current signal on the node 1 output of op-amp U5 in response to receiving a stimulation signal from the conductive tip TP2. In the illustrated embodiment, the stimulation signal may travel from the conductive tip TP2 to node 2 of the transformer T1 via node 1 of the transformer T1.

In one embodiment, the sample and hold circuit is coupled between the diode element (e.g., D7) and the buffer circuit and the diode element is coupled between the secondary side of the transformer and the sample and hold circuit. In the illustrated embodiment, the sample and hold circuit includes resistors R26 and capacitor C11.

In one embodiment, the microcontroller 434 is coupled to receive the peak treatment current signal (SENSE) from the peak detector and coupled to the stimulation driver stage for adjusting the stimulation voltage in response to the peak treatment current signal. In one embodiment, the microcontroller 434 dynamically adjusts the stimulation voltage to keep the peak treatment current signal at a constant value. In one embodiment, microcontroller 434 includes ADC 593 coupled to sample the peak treatment current signal and drive the digital instruction to the DAC U6 (via MOSI communication channel) to keep the peak treatment current signal at the constant value.

The sinus treatment circuitry 500 of FIG. 5 provides a means to maintain a nearly constant (and comfortable) treatment current in response to varying resistance or impedance. Turning to a more specific description of an embodiment of sinus treatment circuitry 500, a digital-to-analog converter (DAC) U6 receives commands from the microcontroller 434 to generate a square wave with a variable amplitude of 0 to +Vcc volts. The DAC U6 output is current limited by R22 and is used to drive a push-pull output power stage comprised of Q5 and Q6, in the illustrated embodiment. The output of the push-pull stage is AC coupled by capacitor C10 and drives the primary side of a step-up transformer T1. Capacitor C10 blocks the DC component of the square wave and allows through only the rising and falling edges of the square wave. The transformer T1 converts the high current, low voltage edge input to the high voltage, low (microcurrent) treatment current output, in the illustrated embodiment.

One end of the secondary side of the transformer is connected to the conductive tip 108. The other end of the secondary coil is connected to a dual diode array D7. The diode array acts as the treatment current positive peak detector. Resistor R26 and capacitor C11 provide a simple sample and hold function of the detected peak. The peak detector output is buffered by op-amp U5. The output of the op-amp U5 is then sampled by the ADC 593 of the microcontroller 434.

During use, a control loop is formed by the DAC U6, peak detector, and the microcontroller 434 ADC 593. The sensed positive peaks of the treatment current are maintained at a constant level by controlling the DAC U6 output. As the total resistance decreases, the control loop reduces the DAC U6 output which reduces the amplitude of the edges being input to the transformer T1. The control loop effectively converts the voltage source output of the transformer T1 to a constant current source, in the illustrated embodiment. In this manner, any uncomfortable surges in current are reduced during treatment.

Figure 6:
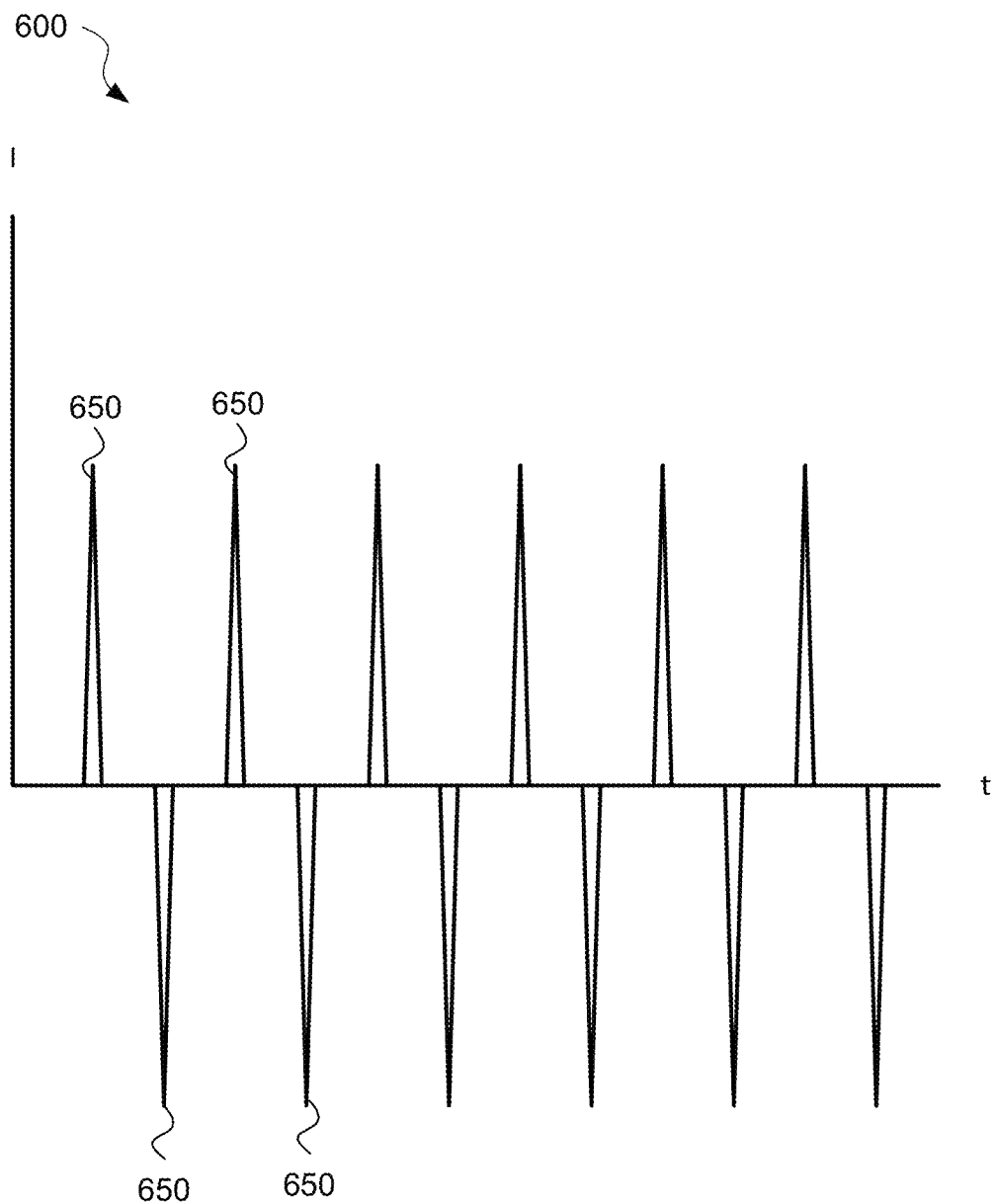
FIG. 6 is a graph of a treatment current vs time, according to an embodiment of the disclosure.

FIG. 6 is a graph 600 of a treatment current (I) vs time (t), according to an embodiment. The treatment current is applied during a treatment mode of the handheld sinus treatment device 102 after the handheld sinus treatment device 102 has identified a treatment location 228. The treatment current provides relief to sinus discomfort and users.

According to an embodiment, the treatment current corresponds to a series of sharp current spikes 650 or peaks. According to an embodiment, successive current spikes 650 alternate in direction such that every other current spike 650 flows in a first direction, while intervening current spikes 650 flow in a second, opposite, direction.

According to an embodiment, the current spikes 650 correspond to the rising and falling edges of a square wave voltage signal. In one embodiment, the treatment current is generated by feeding a square wave voltage signal to a transformer, such as the transformer T1, via a capacitor, such as the capacitor C10. Those of skill in the art will recognize, in light of the present disclosure, that a treatment current in accordance with FIG. 6 can be generated in various ways. All such other ways for generating the treatment current fall within the scope of the present disclosure.

In one embodiment, the treatment current has no DC offset. The lack of a DC offset can enhance the therapeutic effect of the treatment current. This is because, in one interpretation, the rapid changes in current magnitude and direction promote physiological effects that do not occur in the presence of a DC current.

In one embodiment, the sinus treatment circuitry 429, including the microcontroller 434 and the memory 432, adjust the stimulation voltage between the conductive tip 108 and the return electrode 110 to maintain a constant treatment current during the treatment mode. In one embodiment, maintaining a constant treatment current corresponds to causing the current spikes 650 or peaks of the treatment current to have substantially the same magnitudes. In one embodiment, maintaining a constant treatment current corresponds to causing the current spikes 650 or peaks of the treatment current to have substantially the same absolute values. Thus, the positive current peaks 650 and the negative current peaks 650 have the same absolute value, in one embodiment. Alternatively, maintaining a constant treatment current corresponds to causing the positive current spikes 650 or peaks to have a same first magnitude, and causing the negative current spikes 650 or peaks to have a same second magnitude.

In one embodiment, the current spikes 650 or peaks of the sinus treatment current have a magnitude less than or equal to 1000 μA. In one embodiment, the current spikes 650 or peaks of the sinus treatment current have a magnitude less than or equal to 600 μA. In one embodiment, the peaks of the treatment current spikes 650 or peaks have a magnitude less than or equal to 600 μA. In one embodiment, the sinus treatment current spikes 650 have an average current less than or equal to 1000 μA. In one embodiment, the sinus treatment current spikes 650 have an average current less than or equal to 600 μA.

In one embodiment, the frequency of the treatment current is less than 1000 Hz. In one embodiment, the period of a single treatment current cycle corresponds to the time between current peaks 650 of the same direction. In one embodiment, the frequency of the treatment current is between 1 Hz and 100 Hz. In one embodiment, the spikes in the treatment current 650 make up less than 10% of a single cycle. In one embodiment, the spikes in the treatment current 650 make up less than 5% of a single cycle. In one embodiment, the spikes in the treatment current 650 make up about 3% of a single cycle.

In one embodiment, during the treatment mode, the handheld sinus treatment device 102 measures the impedance by measuring the current spikes 650 or peaks of the treatment current. In one embodiment, the handheld sinus treatment device 102 adjusts a stimulation voltage applied between the conductive tip 108 and the return electrode 110 to bring the magnitude of the current spikes 650 or peaks of the treatment current back to a desired constant value.

Those of skill in the art will recognize, in light of the present disclosure, that in practice the treatment current may vary from the graph 600. For example, the risetime and fall time of a given current spike 650 may not be identical. The rise times and fall times of separate current spikes 650 may not be identical to each other. A given current spike 650 can include, at the tail end, a brief portion that flows in the opposite direction to the primary direction of the current spike 650. In a constant current situation, the current spikes 650 may have slightly differing magnitudes while remaining substantially the same. There may be noise present among the current waveform. All such variations from the graph 600 fall within the scope of the present disclosure.

In one embodiment, in the detection mode in which the handheld sinus treatment device 102 identifies treatment locations 228, the handheld sinus treatment device 102 measures the impedance by applying a detection current with a waveform similar or identical to the treatment current waveform and measuring the magnitude of the current peaks of the detection current in order to determine the impedance. In one embodiment, the handheld sinus treatment device 102 measures the impedance by passing a detection current with a smaller magnitude than the treatment current. In one embodiment, during the detection mode, the handheld sinus treatment device 102 applies a detection voltage that is lower than the stimulation voltage applied during the treatment mode. In one embodiment, the handheld sinus treatment device 102 measures the impedance by passing a detection current with a waveform entirely different than the treatment current waveform.

Figure 7:
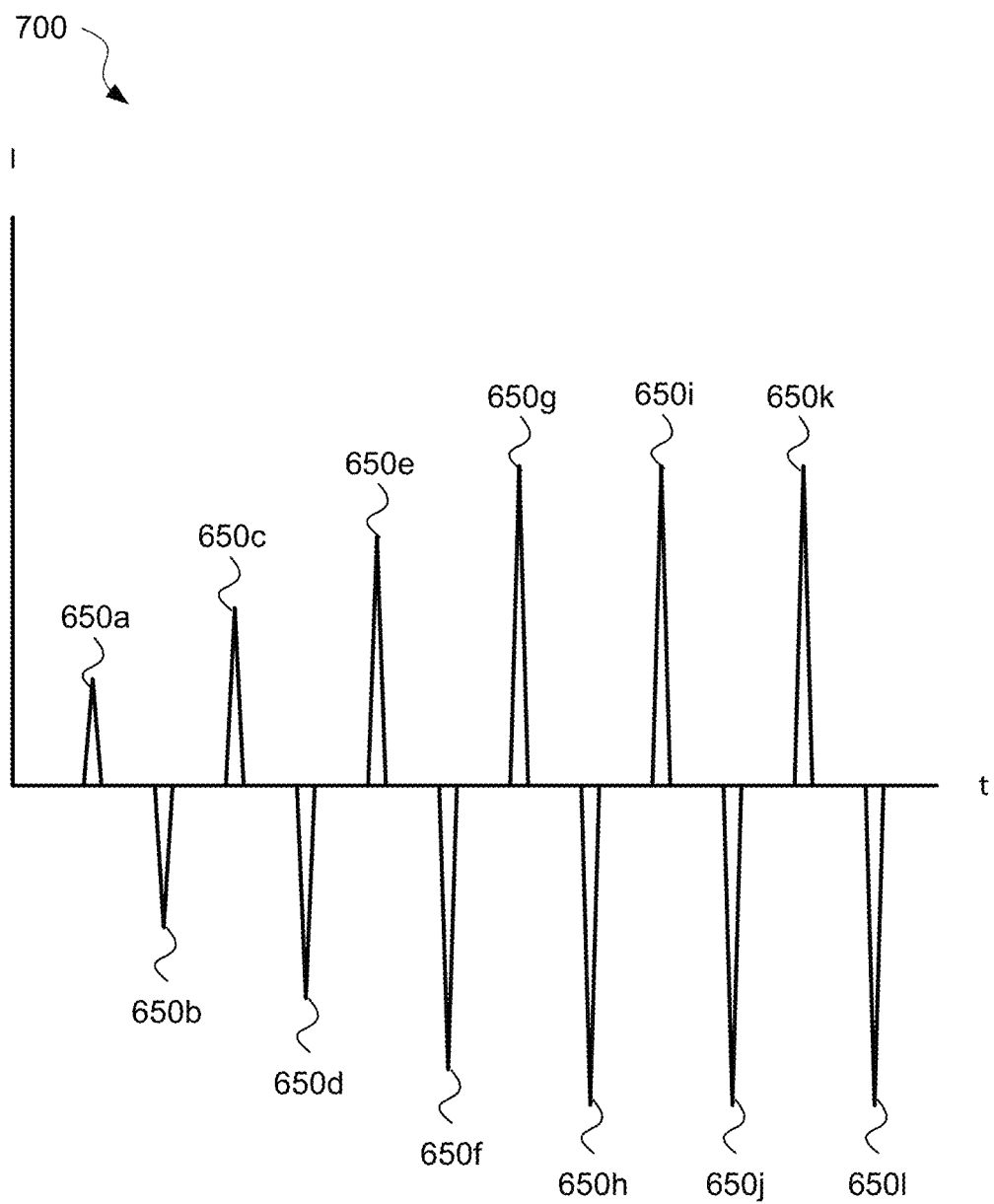
FIG. 7 is a graph of a treatment current vs time including a gradually increasing treatment current, according to an embodiment of the disclosure.

FIG. 7 is a graph 700 of a treatment current (I) vs time (t), according to an embodiment. Similar to the graph 600 of FIG. 6, the treatment current includes a series of current spikes 650. The treatment current is passed between the conductive tip 108 and the return electrode 110 through the body of the user during the treatment mode of the handheld sinus treatment device 102.

In order to promote the further comfort of the user during the treatment mode, the magnitude of the treatment current is gradually increased during the treatment mode. In particular, at the beginning of the treatment mode, successive current spikes 650 increase in magnitude until the treatment current has arrived at the full treatment level. In this way, during the treatment mode, the user does not immediately receive the full magnitude of the current spikes 650, but rather the magnitude of the current spikes 650 gradually increased in a comfortable manner to a full treatment level.

In one embodiment, a first current spike 650*a* has a magnitude that is much smaller than a full treatment level. A second current spike 650*b* has a magnitude or absolute value that is greater than the magnitude of the first current spike 650*a*, though in the opposite direction. A third current spike 650*c* has a magnitude or absolute value that is greater than the second current spike 650*b*. A fourth current spike 650*d* has a magnitude or absolute value that is greater than the third current spike 650*c*. A fifth current spike 650*e* has a magnitude or absolute value that is greater than the fourth current spike 650*d*. A sixth current spike 650*f* has a magnitude or absolute value that is greater than the fifth current spike 650*e*. A seventh current spike 650*g* has a magnitude or absolute value that is greater than the sixth current spike 650*f*. The magnitude of the seventh current spike 650*g* corresponds to the full treatment level. In one embodiment, all of the successive current spikes 650*h*-650*i* that follow the seventh current spike 650*g* have a same magnitude or absolute value corresponding to the full treatment level. The treatment mode for a given treatment location 228 can include a much larger number of current spikes 650 than are shown in the graph 700 depending on the duration of the treatment mode and the frequency of the treatment current.

In one embodiment, the current spikes 650 in a first direction ramp up to a first direction full treatment level, while the current spikes 650 in the second direction ramp up to a second direction full treatment level different than the first direction full treatment level.

In one embodiment, after the treatment current has been applied to a treatment location 228 and identified during a treatment mode, the user proceeds to locate the next treatment location 228 during a subsequent detection mode. When the user has located the next treatment location 228, the handheld sinus treatment device 102 applies a treatment current that ramps up to a full treatment level similar to the previous treatment mode.

Figure 8:
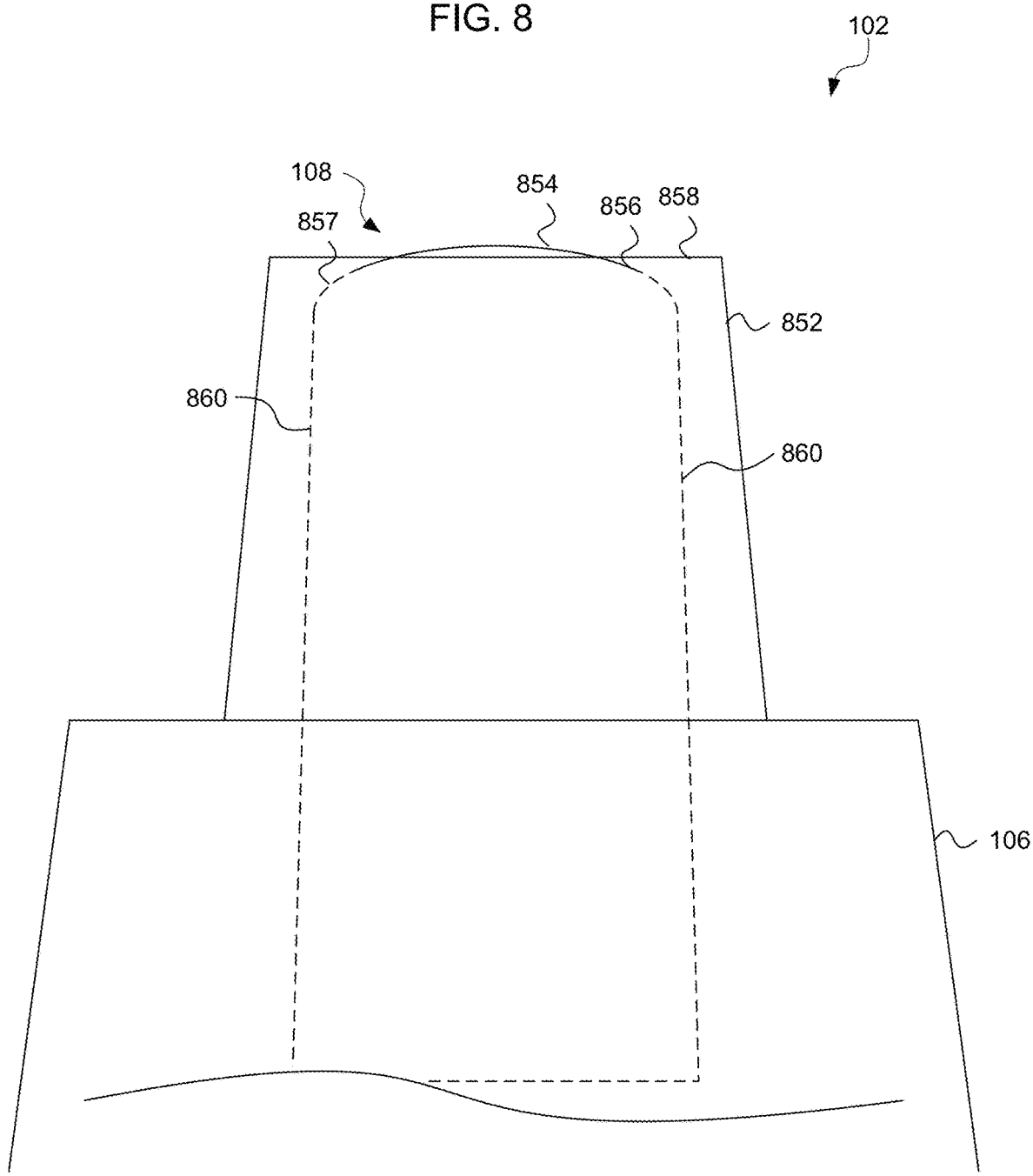
FIG. 8 is an enlarged view of a portion of a sinus treatment device, according to an embodiment of the disclosure.

FIG. 8 is an enlarged view of a portion of the handheld sinus treatment device 102, according to one embodiment. The conductive tip 108 extends from the housing 106. The conductive tip 108 includes a distal surface 856 distal from the housing 106. The conductive tip 108 includes a columnar portion 860 that extends towards distal surface 856. The distal surface 856 is configured to be placed on the face 226 of the user to detect treatment locations 228 and to apply the treatment current.

In one embodiment, the handheld sinus treatment device 102 includes a dielectric covering 852 positioned on the conductive tip 108. The dielectric covering 852 is positioned on the conductive tip 108 in such a way that a portion of the distal surface 856 is covered by the dielectric covering 852 and a portion of the distal surface 856 is uncovered by the dielectric covering 852. Thus, according to an embodiment, the dielectric covering 852 defines a covered portion 857 of the distal surface 856 and an exposed portion 854 of the distal surface 856. The dielectric covering 852 also includes a distal surface 858 distal to the housing 106. The distal surface 858 can also be considered a top surface of the dielectric covering 852, according to one embodiment.

In one embodiment, the dielectric covering 852 is positioned so that the distal surface 858 of the dielectric covering 852 is in contact with the face 226 of the user when the exposed portion 854 is in contact with the face 226 of the user. Thus, while the user uses the handheld sinus treatment device 102 to detect treatment locations 228 and to apply the treatment current, both the exposed portion 854 of the conductive tip 108 and the distal surface 858 of the dielectric covering 852 are in contact with the face 226 of the user.

In one embodiment, it can be beneficial for the treatment current to have a high current density at the treatment location 228 such that the nerve node receives a high current density. In order to promote a high current density at the treatment location 228, it is beneficial for a relatively small surface area of the conductive tip 108 to contact the user's face 226 at the treatment location 228. One way to ensure a relatively small surface area of the conductive tip 108 contacts the user's face 226 during treatment is to have a conductive tip 108 that is relatively sharp at the point of contact. However, this can promote great discomfort in the user. In some cases, such a sharp conductive tip 108 could scratch, pierce, or otherwise induce pain or damage at the treatment location 228.

In one embodiment, in order to avoid discomfort, the conductive tip 108 includes a distal end 856 that is very gently rounded such that the user does not experience discomfort when placing the conductive tip 108 on the face 226 of the user. As set forth above, without taking other measures, such a gently rounded conductive tip 108 could decrease the current density at the treatment location 228 because the larger surface area of the conductive tip 108 would be in contact with the user's face 226.

In one embodiment, the presence and configuration of the dielectric covering 852 enhances the comfort of the user while also enabling a relatively high current density at the treatment location 228 or nerve node. In particular, the distal surface 856 is rounded such that the distal surface 856 has a relatively low radius of curvature. Nevertheless, the dielectric covering 852 covers a portion of the distal surface 858 such that during use of the handheld sinus treatment device 102, only the exposed portion 854 of the distal surface 856 is in contact with the face 226 of the user. The exposed portion 854 is rounded with a low radius of curvature. The distal surface 858 of the dielectric covering 852 will also be in contact with the face 226 of the user during use of the handheld sinus treatment device 102. Because only an exposed portion 854 of the distal surface 856 is in contact with the face 226 of the user, relatively high current density is maintained during the treatment mode at the treatment location 228. Because the distal surface 856 is rounded, the user does not experience discomfort when the conductive tip 108 is placed on the face 226 of the user.

In FIG. 8, portions of the conductive tip 108 that are covered by the dielectric covering 852 and the housing 106 are shown in dashed lines.

In one embodiment, the dielectric covering 852 covers a portion of the columnar portion 860 of the conductive tip 108. In one embodiment, the housing 106 covers a columnar portion 860 of the conductive tip 108. In one embodiment, the dielectric covering 852 is positioned on and in contact with the housing 106. In one embodiment, the distal surface 858 of the dielectric covering 852 is rounded to promote comfort for the user while using the handheld sinus treatment device 102.

In one embodiment, the conductive tip 108 includes a material that is electrically conductive while having a lower thermal conductivity than traditional electrical conductors such as copper, gold, silver, iron, aluminum, titanium, and other common metal alloys that are electrically conductive. Such traditional conductive materials also have relatively high thermal conductivities. Such high thermal conductivity can cause discomfort when the material is placed on the skin of the user. If a material with high thermal conductivity is relatively cold compared to the skin of the user, the material will feel colder than would a material with lower thermal conductivity but at the same temperature as the material with higher thermal conductivity. Likewise, if a material high thermal conductivity is relatively hot compared to the skin of the user, the material will feel hotter on the skin of the user than would a material with lower thermal conductivity without the same temperature as the material of higher thermal conductivity. Accordingly, in one embodiment, the conductive tip 108 includes a material that is both electrically conductive while having a relatively low thermal conductivity with respect to traditional conductors.

In one embodiment, the conductive tip 108 includes a conductive polymer. The conductive polymer has a low thermal conductivity compared to typical electrical conductors. The conductive polymer is also electrically conductive such that the treatment current can be applied between the conductive tip 108 and the return electrode 110. In one embodiment, the conductive polymer includes one or more of polyacetylene, polyethylene vinylene, polypyrrole, polythiophene, polyaniline, and polyphenylene sulfide. Those of skill in the art will recognize, in light of the present disclosure, that the conductive tip 108 can include other materials that are electrical conductors with relatively low thermal conductivity. All such other materials fall within the scope of the present disclosure.

In one embodiment, the dielectric covering 852 includes a plastic material. In one embodiment, the dielectric covering 852 includes a ceramic material. In one embodiment, the dielectric covering 852 includes an epoxy material. In one embodiment, the dielectric covering 852 includes a rubber material.

In one embodiment, the conductive tip 108 includes an electrical conductor including one or more of aluminum, titanium, gold, silver, iron, or other conductive metals, metal alloys, or other kinds of conductive materials.

Figure 9A:
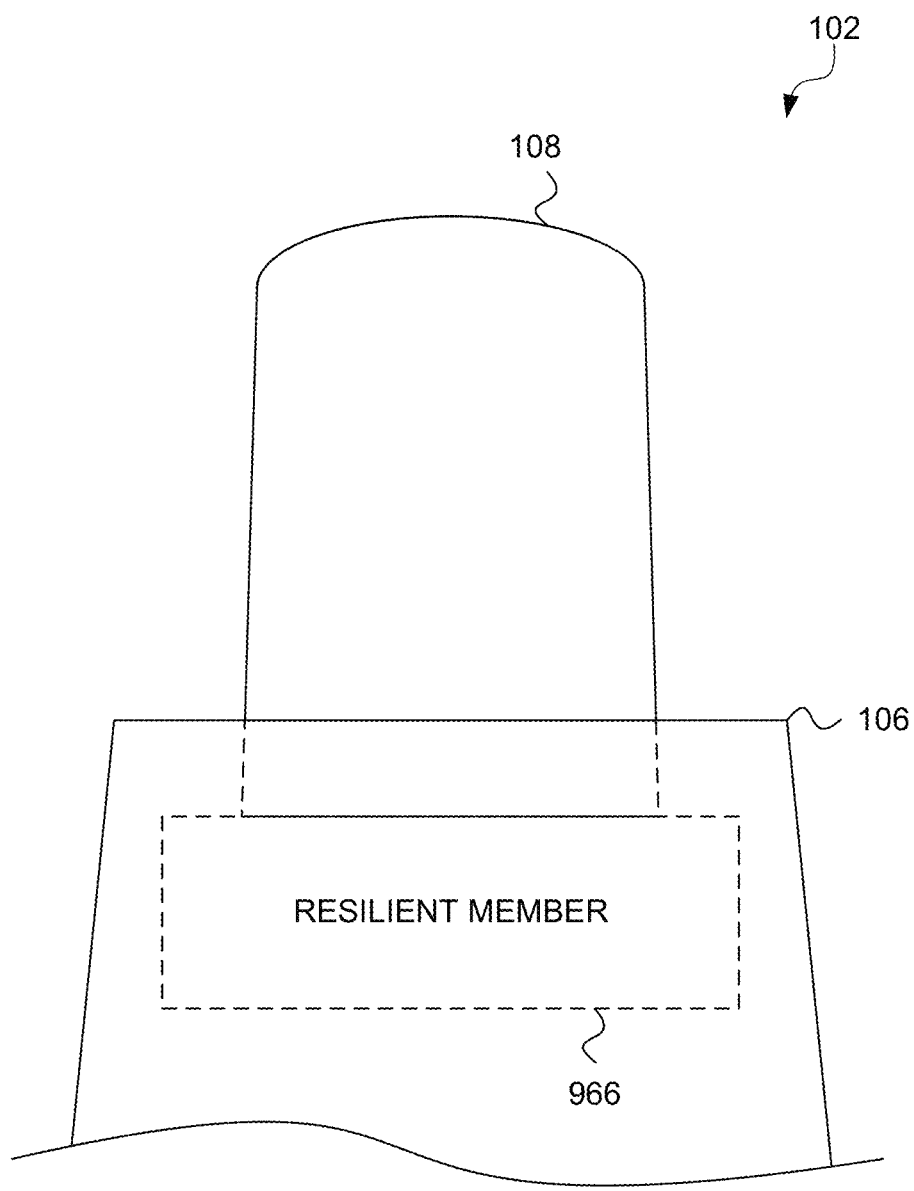
FIG. 9A is an enlarged view of a portion of a sinus treatment device including a resilient member, according to an embodiment of the disclosure.

FIG. 9A is an illustration of a portion of a handheld sinus treatment device 102 including a resilient member 966, according to one embodiment. The resilient member 966 is coupled to the conductive tip 108 and the housing 106 in such a way that the conductive tip 108 resiliently depresses toward the housing 106 when pressure or force is applied to the conductive tip 108. When the pressure or force is no longer applied to the conductive tip 108, the resilient member 966 returns to an equilibrium position, thereby causing the conductive tip 108 return to the equilibrium position.

In some cases, if a user accidentally presses the conductive tip 108 against the skin of the user with too much force, the user could feel discomfort at that location if the conductive tip 108 is rigidly positioned relative to the housing 106. Accordingly, in order to further enhance the comfort of the user, the handheld sinus treatment device 102 includes the resilient member 966 coupled to the conductive tip 108 in the housing 106. When the user presses the conductive tip 108 against the skin of the user, the resilient member 966 flexes in a way that enables the conductive tip 108 to depress toward the housing 106. Thus, if the user accidentally applies a larger than normal amount of force when pressing the conductive tip 108 against the skin, the user will not experience discomfort because the conductive tip 108 will depress downward due to the coupling with the resilient member 966.

In one embodiment, the resilient member 966 is positioned within the housing 106. The resilient member 966 is in contact with a portion of the conductive tip 108 that is also positioned within the housing 106. The resilient member 966 is coupled to the conductive tip 108 and configured to enable the conductive tip 108 to resiliently depress toward the housing 106. Because a portion of the conductive tip 108 may be positioned within the housing 106, depression of the conductive tip 108 toward the housing 106 can correspond to a distal surface 856 or treatment surface of the conductive tip 108 the pressing toward the housing 106.

In one embodiment, the resilient member 966 is positioned external to the housing 106. For example, the resilient member 966 can be positioned on an upper surface of the housing 106 between the housing 106 and the conductive tip 108. In this case, electrical connections to the conductive tip 108 may couple to the conductive tip 108 external to the housing 106. Because the entirety of the conductive tip 108 may be positioned external to the housing 106, depression of the conductive tip 108 toward the housing 106 can correspond to depression of the entire conductive tip 108 toward the housing 106.

In one embodiment, the resilient member 966 includes a spring. When pressure is applied to the conductive tip 108, the pressure causes the spring to compress such that the conductive tip 108 depresses or moves toward the housing 106. When the pressure is no longer applied to the conductive tip 108, the spring decompresses and the conductive tip 108 extends from the housing 106 to a rest position.

In one embodiment, the resilient member 966 includes a flexible membrane. When pressure is applied to the conductive tip 108, the pressure causes the flexible membrane to deform in a direction away from the face 226 of the user. The conductive tip 108 in turn depresses toward the housing 106. When the pressure is no longer applied to the conductive tip 108, the flexible membrane returns to an equilibrium position and the conductive tip 108 extends from the housing 106 toward an equilibrium position.

In one embodiment, the resilient member 966 includes an elastic material. In one embodiment, the resilient member 966 includes rubber. Other resilient materials, configurations, and structures can be selected for the resilient member 966 without departing from the scope of the present disclosure.

Figure 9B:
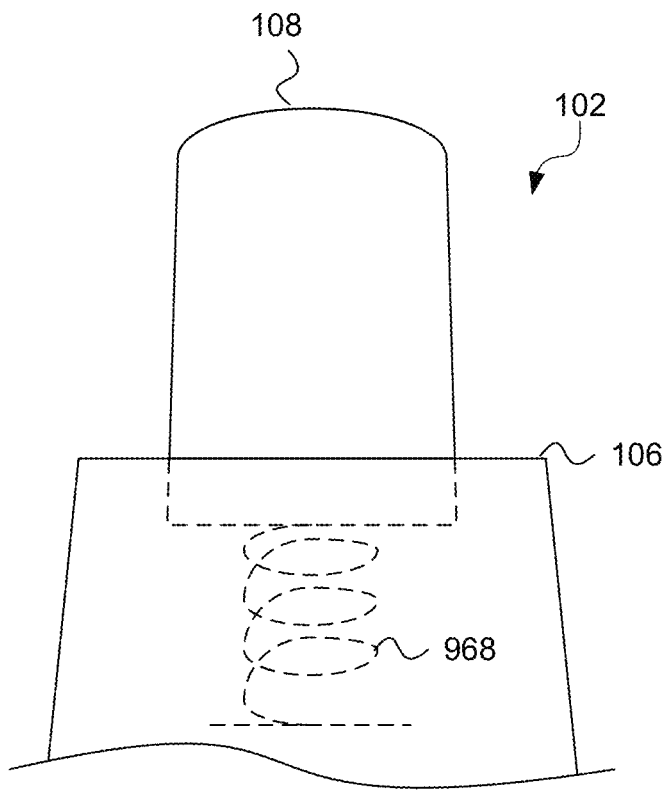
FIGS. 9B and 9C are enlarged views of a portion of a sinus treatment device including a spring, according to an embodiment of the disclosure.
Figure 9C:
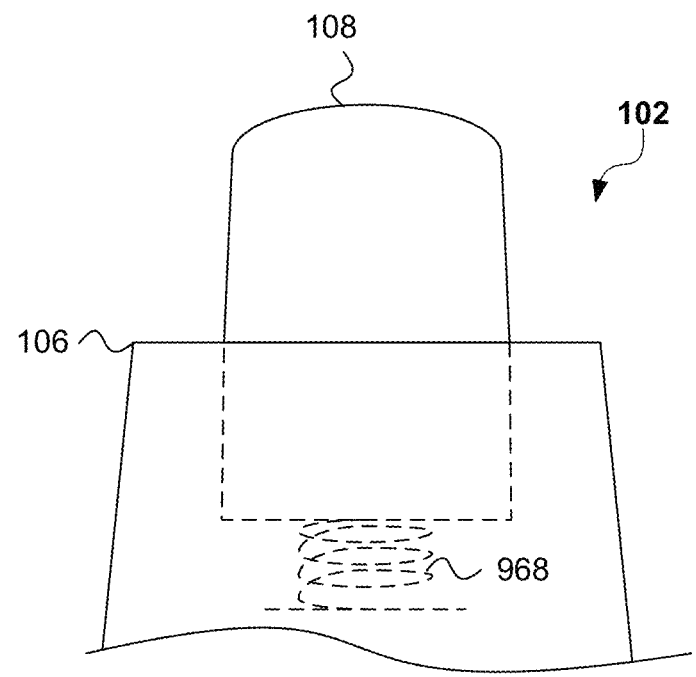

FIGS. 9B and 9C are illustrations of a portion of handheld sinus treatment device 102 including a spring 968, according to one embodiment. The spring 968 is coupled to the housing 106 and the conductive tip 108 in such a way that enables the conductive tip 108 to depress toward the housing 106 when pressure or force is applied to the conductive tip 108. FIG. 9A is an illustration of the handheld sinus treatment device 102 in a condition in which external force or pressure is not applied to the conductive tip 108, such that the conductive tip 108 and the spring 968 are in equilibrium position. FIG. 9B is an illustration of the handheld sinus treatment device 102 in a condition in which external force or pressure is applied to the conductive tip 108, such that the spring 968 is compressed and the conductive tip 108 has depressed toward the housing 106.

In one embodiment, the spring 968 is positioned internally within the housing 106. Alternatively, the spring 968 can be positioned external to the housing 106. For example, the spring 968 can be positioned on a top surface of the housing 106 between the housing 106 and the conductive tip 108.

In one embodiment, the spring 968 is an electrical conductor. The spring 968 can electrically couple the conductive tip 108 sinus treatment circuitry positioned within the housing 106 such that when the treatment current passes through the conductive tip 108, the treatment current also passes through the spring 968.

Figure 9D:
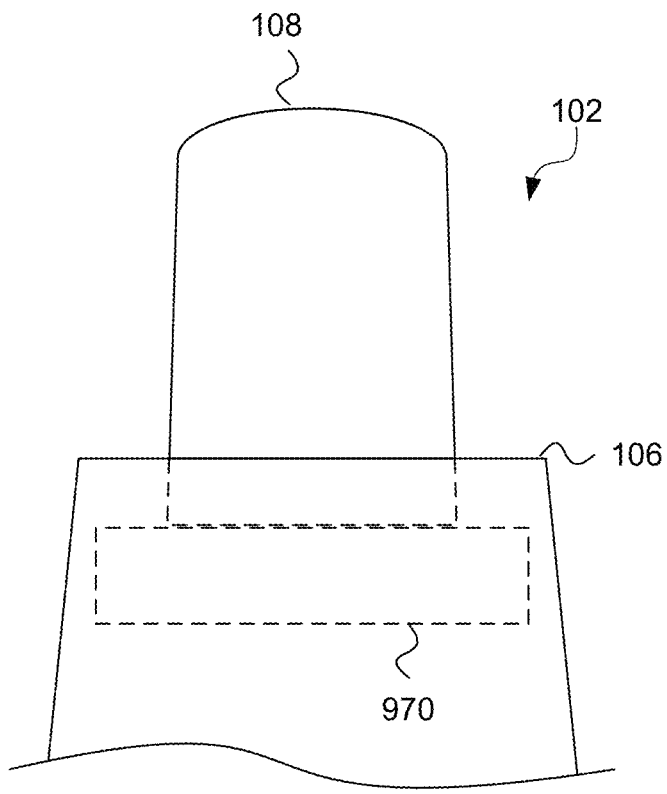
FIGS. 9D and 9E are enlarged views of a portion of a sinus treatment device including a flexible membrane, according to an embodiment of the disclosure.
Figure 9E:
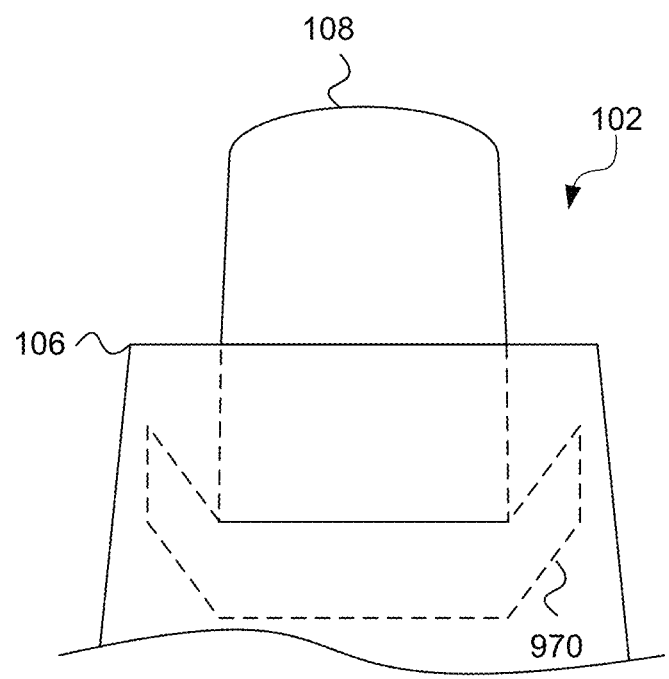

FIGS. 9D and 9E are illustrations of a portion of handheld sinus treatment device 102 including a flexible membrane 970, according to one embodiment. The flexible membrane 970 is coupled to the housing 106 and the conductive tip 108 in such a way that enables the conductive tip 108 to depress toward the housing 106 when pressure or force is applied to the conductive tip 108. FIG. 9D is an illustration of the handheld sinus treatment device 102 in a condition in which external force or pressure is not applied to the conductive tip 108, such that the conductive tip 108 and the flexible membrane 970 are in equilibrium position. FIG. 9E is an illustration of the handheld sinus treatment device 102 in a condition in which external force or pressure is applied to the conductive tip 108, such that the flexible membrane 970 is deformed and the conductive tip 108 has depressed toward the housing 106.

In one embodiment, the flexible membrane 970 is positioned internally within the housing 106. Alternatively, the flexible membrane 970 can be positioned external to the housing 106. For example, the flexible membrane 970 can be positioned on a top surface of the housing 106 between the housing 106 and the conductive tip 108.

In one embodiment, the flexible membrane 970 is an electrical conductor. The flexible membrane 970 can electrically couple the conductive tip 108 sinus treatment circuitry positioned within the housing 106 such that when the treatment current passes through the conductive tip 108, the treatment current also passes through the flexible membrane 970.

Figure 10:
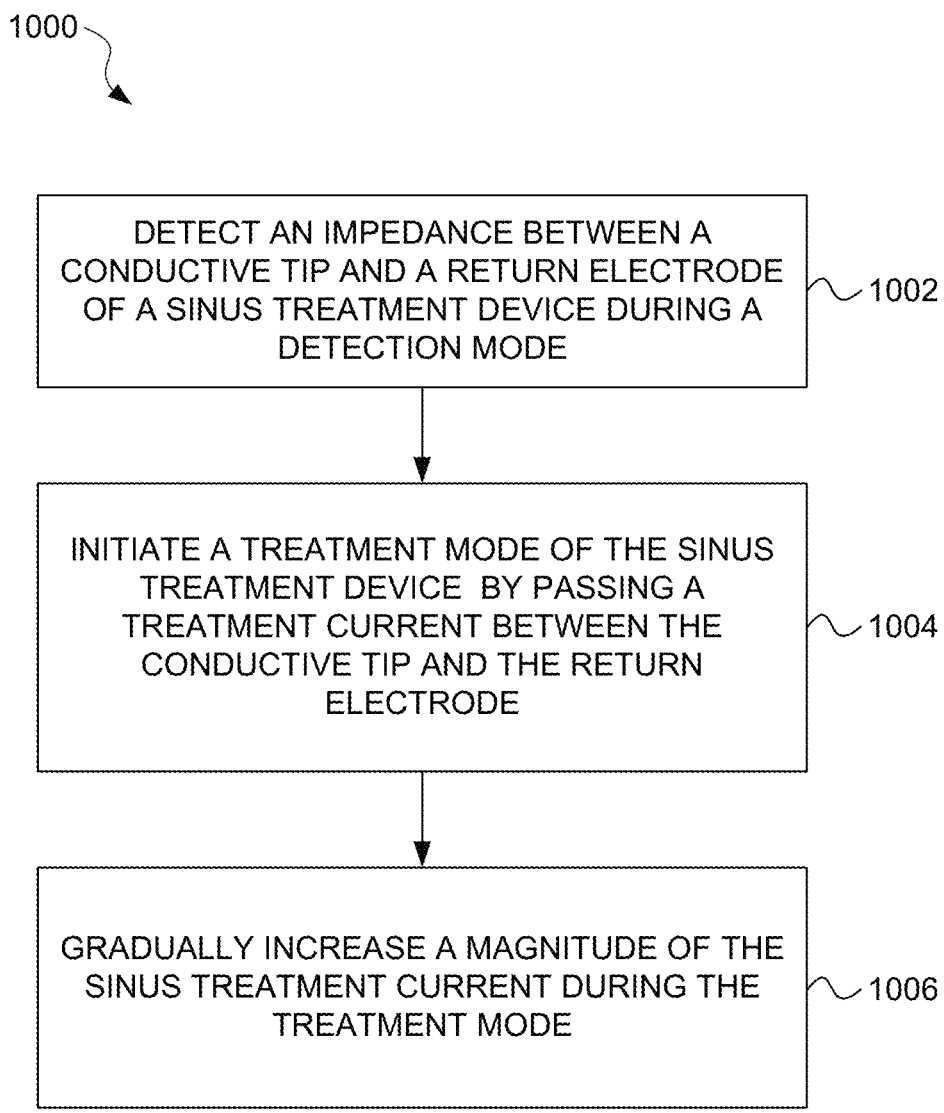
FIG. 10 is a flow chart of a process for operating a sinus treatment device, according to an embodiment of the disclosure.

FIG. 10 is a flow chart illustrating a process 1000 of operating a sinus treatment device, according to an embodiment of the disclosure.

At 1002, an impedance is detected between a conductive tip and a return electrode of a sinus treatment device, according to one embodiment.

At 1004, a treatment mode of the sinus treatment device is initiated by passing a treatment current between the conductive tip and the return electrode, according to one embodiment.

At 1006, a magnitude of the treatment current is gradually increased during the treatment mode, according to one embodiment.

Figure 11:
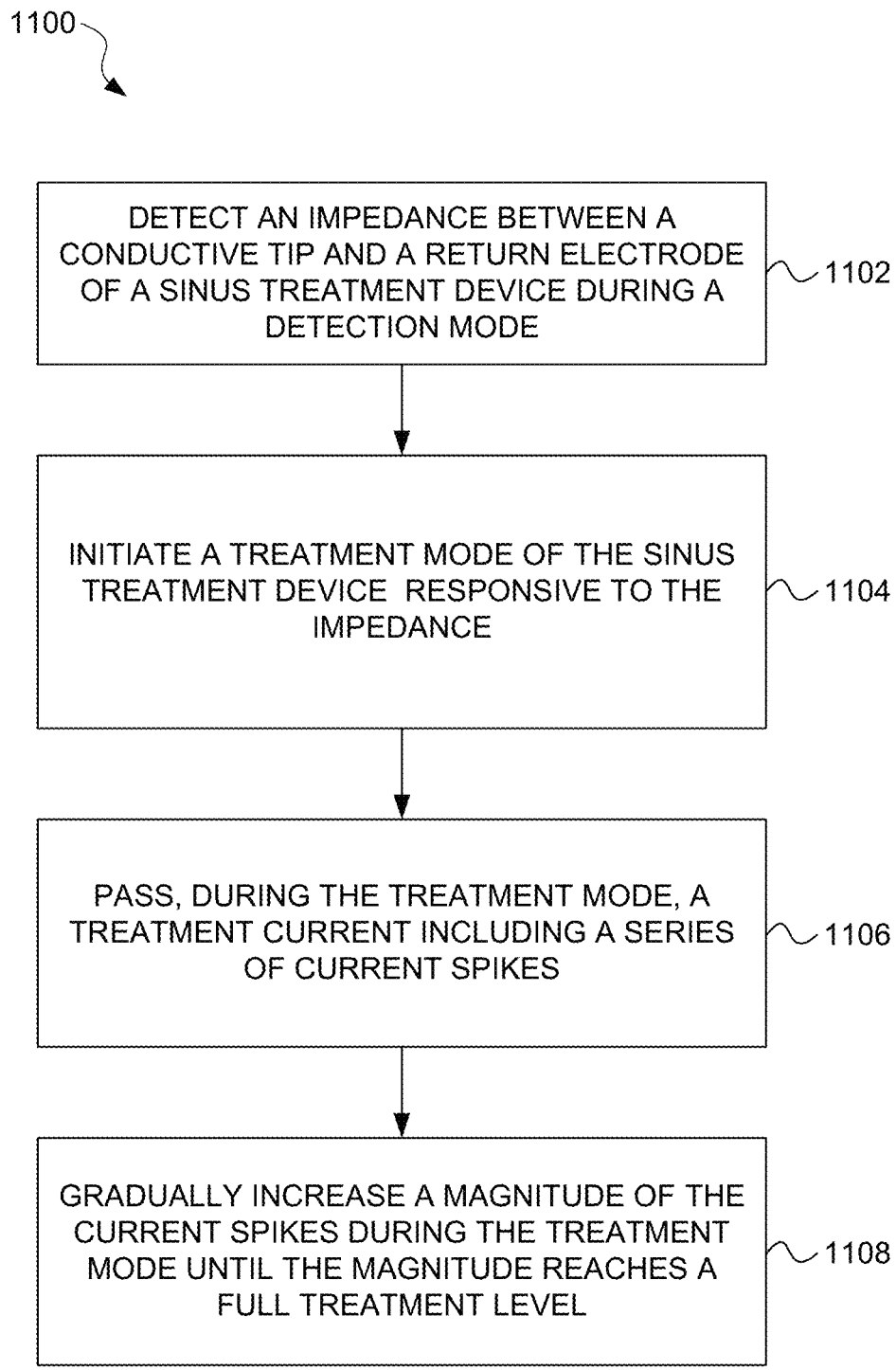
FIG. 11 is a flow chart of a process for operating a sinus treatment device, according to an embodiment of the disclosure.

FIG. 11 is a flow chart illustrating a process 1100 of operating a sinus treatment device, according to an embodiment of the disclosure.

At 1102, an impedance is detected between a conductive tip and a return electrode of a sinus treatment device, according to one embodiment.

At 1104, a treatment mode of the sinus treatment device is initiated responsive to the impedance, according to one embodiment.

At 1106, a treatment current including a series of current spikes is passed between the conductive tip and the return electrode during the treatment mode, according to one embodiment.

At 1108, a magnitude of the current spikes is gradually increased during the treatment mode until the magnitude reaches a full treatment level, according to one embodiment.

In one embodiment, an initial stimulation voltage of the treatment mode driven across the conductive tip (e.g., 108) and the return electrode (e.g., 110) is a user selected stimulation voltage received from a user input of the handheld sinus treatment device (e.g., 102).

In one embodiment, a method includes initiating a haptic feedback of the handheld sinus treatment device (e.g., 102) when the treatment mode is initiated.

In one embodiment, a method includes illuminating a light emitting diode of the handheld sinus treatment device (e.g., 102) when the treatment mode is initiated.

In one embodiment, the return electrode (e.g., 110) is attached to a body (e.g., 106) of the handheld sinus treatment device (e.g., 102) that is formed to be held by a hand of a user of the handheld sinus treatment device (e.g., 102) and the return electrode (e.g., 110) is exposed to contact the hand of the user. In one embodiment, the return electrode (e.g., 110) is included in a body (e.g., 106) of the handheld sinus treatment device (e.g., 102), and wherein the body (e.g., 106) includes conductive polycarbonate to serve as the return electrode (e.g., 110).

In one embodiment, the process 1100 further includes turning off the handheld sinus treatment device (e.g., 102) when the impedance between the conductive tip (e.g., 108) and the return electrode (e.g., 110) is over a pre-determined threshold for a pre-determined time period (e.g., 2 minutes).

In one embodiment of the process 1100, driving the stimulation voltage across the conductive tip (e.g., 108) and the return electrode (e.g., 110) includes driving voltage pulses across the conductive tip (e.g., 108) and the return electrode (e.g., 110).

In one embodiment, the conductive tip (e.g., 108) is a spring-loaded tip to reduce the pressure of the conductive tip (e.g., 108) on a sinus skin area of the user of the handheld sinus treatment device (e.g., 102). In one embodiment, the conductive tip (e.g., 108) includes a conductor and a dielectric tip and both the conductor and the dielectric tip contact a sinus skin area of the user when the conductive tip (e.g., 108) is applied to the sinus skin area of the user. In one embodiment, the conductor includes carbon fiber.

In one embodiment, a method of operating a handheld sinus treatment device (e.g., 102) includes measuring a stimulation signal from a conductive tip (e.g., 108) of the handheld sinus treatment device (e.g., 102) where the stimulation signal is representative of a treatment current between the conductive tip (e.g., 108) and a return electrode (e.g., 110) attached with a body (e.g., 106) of the handheld sinus treatment device (e.g., 102). The process further includes dynamically adjusting a stimulation voltage across the conductive tip (e.g., 108) and the return electrode (e.g., 110) to keep the treatment current at a constant value in response to measuring the stimulation signal.

According to an embodiment, a method of operating a handheld sinus treatment device (e.g., 102) includes detecting an impedance between a conductive tip (e.g., 108) of the handheld sinus treatment device (e.g., 102) and a return electrode (e.g., 110) of the handheld sinus treatment device (e.g., 102). The method includes initiating a treatment mode of the handheld sinus treatment device (e.g., 102) when the impedance drops below a threshold by applying a stimulation voltage between the conductive tip (e.g., 108) and the return electrode (e.g., 110). The method includes changing the stimulation voltage as the impedance between the conductive tip (e.g., 108) and the return electrode (e.g., 110) changes during the treatment mode.

According to an embodiment, a method includes applying, with a handheld sinus treatment device (e.g., 102), sinus treatment stimulation to a sinus treatment location (e.g., 228) of a user by applying a treatment current between a conductive tip (e.g., 108) and a return electrode (e.g., 110) of the handheld sinus treatment device (e.g., 102). The method includes measuring a stimulation signal representative of the treatment current and maintaining a constant value of the treatment current during the treatment mode by dynamically adjusting a stimulation voltage between the conductive tip (e.g., 108) and the return electrode (e.g., 110) in response to measuring the stimulation signal.

According to an embodiment, a method of operating a handheld sinus treatment device (e.g., 102) includes initiating a treatment mode of the handheld sinus treatment device (e.g., 102) by applying a stimulation voltage between a conductive tip (e.g., 108) of a handheld sinus treatment device (e.g., 102) and a return electrode (e.g., 110) of the handheld sinus treatment device (e.g., 102). The method includes changing the stimulation voltage as an impedance between the conductive tip (e.g., 108) and the return electrode (e.g., 110) changes during the treatment mode.

According to an embodiment, a handheld sinus treatment device (e.g., 102) includes a conductive tip (e.g., 108), a return electrode (e.g., 110) operatively coupled to a body (e.g., 106) of the handheld sinus treatment device (e.g., 102), and a stimulation driver stage coupled to apply a stimulation voltage between the conductive tip (e.g., 108) and the return electrode (e.g., 110). The handheld sinus treatment device (e.g., 102) includes a peak detector coupled to generate a peak treatment current signal in response to receiving a stimulation signal from the conductive tip (e.g., 108). The handheld sinus treatment device (e.g., 102) includes a microcontroller (e.g., 434) coupled to receive the peak treatment current signal from the peak detector and coupled to the stimulation driver stage for adjusting the stimulation voltage in response to the peak treatment current signal. The microcontroller (e.g., 434) dynamically adjusts the stimulation voltage to keep the peak treatment current signal at a constant value.

According to an embodiment, a handheld sinus treatment device (e.g., 102) includes a body (e.g., 106) configured to be held in a hand of user, a conductive tip (e.g., 108) coupled to the body (e.g., 106), and a return electrode (e.g., 110) positioned on the body (e.g., 106) such that when a user holds the body (e.g., 106) the hand of the user is in contact with the return electrode (e.g., 110). The handheld sinus treatment device (e.g., 102) includes sinus treatment circuitry positioned within the body (e.g., 106) and configured to detect an impedance between the conductive tip (e.g., 108) and the return electrode (e.g., 110) and to enter a treatment mode responsive to the impedance dropping below a threshold by applying a treatment current between the conductive tip (e.g., 108) and the return electrode (e.g., 110).

According to an embodiment, a method includes detecting, during a detection mode, an impedance between a conductive tip (e.g., 108) of a sinus treatment device (e.g., 102) and a return electrode (e.g., 110) of the sinus treatment device (e.g., 102). The method includes initiating a treatment mode of the sinus treatment device (e.g., 102) when the impedance drops below a threshold including passing a treatment current between the conductive tip (e.g., 108) and the return electrode (e.g., 110). The treatment current includes a series of current spikes (e.g., 650).

According to an embodiment, a method includes detecting, during a detection mode, an impedance between a conductive tip (e.g., 108) of the sinus treatment device (e.g., 102) and a return electrode (e.g., 110) of the sinus treatment device (e.g., 102). The method includes initiating a treatment mode of the sinus treatment device (e.g., 102) when the impedance drops below a threshold including passing a treatment current between the conductive tip (e.g., 108) and the return electrode (e.g., 110). The treatment current has a magnitude less than 1000 µA.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

FIG. 12 shows several views of a microcurrent sinus treatment device 1200, according to an embodiment.

The inventors note that the device described herein includes several features intended to provide a positive user experience.

With respect to structure, a therapeutic tip may include a screw thread to hold a case together with no external screws.

According to an embodiment, a device includes a metal or metal-coated plastic return electrode on a case structure portion that occupies an area selected to make it nearly impossible for a user to hold the device without completing a circuit. In an embodiment, the device uses metal-plated plastic. In an embodiment, the device uses punched aluminum for the exposed portion of the return electrode.

Referring to FIG. 12, according to an embodiment, a microcurrent sinus treatment device 1200 includes a circuit configured to deliver a sequence of voltage pulses carrying a therapeutic current, and a therapeutic electrode 1204 operatively coupled to the circuit. In an embodiment, the therapeutic electrode 1204 may be configured to apply the sequence of voltage pulses to a user's skin surface adjacent to one of a plurality of nerve nodes subjacent to the user's skin surface. In an embodiment, the therapeutic electrode 1204 may be in electrical continuity with a therapeutic current output node of the circuit. According to an embodiment, the microcurrent sinus treatment device 1200 includes a hand holdable case 1206 configured to substantially contain active portions of the circuit. In an embodiment, the hand holdable case 1206 includes a forward end 1208 terminating in the therapeutic electrode 1204, and a return electrode 1210 comprising a portion of or disposed on a surface of the hand holdable case 1206. In an embodiment, the return electrode 1210 may be in electrical continuity with a current return node of the circuit. In an embodiment, the hand holdable case 1206 includes a dielectric spacer 1212 disposed between the therapeutic electrode 1204 and the return electrode 1210, and a rearward portion 1214 of the hand holdable case 1206 terminating at an end 1220 a distance selected to comfortably fit in an adult human hand, typically less than about four inches from the therapeutic electrode 1204 tip. In an embodiment, the dielectric spacer 1212 and the return electrode 1210 form a tapered surface 1216 narrowing toward the therapeutic electrode 1204 from a point of maximum girth disposed between the forward end 1208 and the rearward end 1220 of the hand holdable case 1206.

According to an embodiment, the therapeutic electrode 1204 is configured to clamp the return electrode 1210 against the rearward portion 1214 of the hand holdable case 1206 to hold the dielectric spacer 1212 and the return electrode 1210 together with the rearward portion 1214 of the hand holdable case 1206. In an embodiment, the therapeutic electrode 1204 includes a threaded portion configured to screw into a hole (not shown) formed inside the rearward portion 1214 of the hand holdable case 1206. In another embodiment, the placement of the therapeutic electrode 1204, the dielectric spacer 1212, and the return electrode 1210 are configured to cause the user's body to complete a circuit between the therapeutic electrode 1204 and the return electrode 1210.

In an embodiment, the tapered case is adaptable to a large range of hand sizes. In an embodiment, the rearward end 1220 of the hand holdable case 1206 is less than three inches from the therapeutic electrode 1204 tip. In an embodiment, the tapered surface 1216 is conducive to cause the user's hand to naturally contact the return electrode 1210. In an embodiment, the tapered surface 1216 is conducive to provide satisfactory control for holding the therapeutic electrode 1204 against the user's skin superjacent to each of the plurality of nerve nodes.

According to an embodiment, in FIG. 12, the hand holdable case 1206 forms a surface having an indentation larger than an average user's thumb on a back side of the hand holdable case 1206 such that a front portion of the indentation extends toward the therapeutic electrode 1204 and away from the point of maximum girth of the hand holdable case 1206. In one embodiment, the indentation is disposed with at least a majority of its area between the therapeutic electrode 1204 and the point of maximum girth. In another embodiment, the indentation is disposed partially extending beyond the point of maximum girth toward the rearward end 1220 of the hand holdable case 1206.

According to an embodiment, the dielectric spacer 1212 defines a concave insulated surface near the therapeutic electrode 1204 to make clearance for the user's cheek and/or nose.

According to an embodiment, the hand holdable case 1206 defines a tapered surface on a top, between the point of maximum girth and the forward end 1208, configured to provide a finger hold. In an embodiment, the tapered surface forms a facet relative to other portions of the top.

According to an embodiment, the hand holdable case 1206 defines a convex curved surface, on the top between the point of maximum girth and the rearward end 1220, configured to fit into a hollow of the user's palm.

According to a embodiment, the hand holdable case 1206 defines a tapered side 1216 to accommodate finger placement.

According to an embodiment, the hand holdable case 1206 further comprises a light pipe 1228 disposed between the forward end 1208 and the return electrode 1210, the light pipe 1228 being configured to output an illumination indicator from a light emitting diode (LED) disposed on the circuit to indicate an operating condition to the user.

According to an embodiment, the microcurrent sinus treatment device 1200 further includes a button 1230 configured to cause the circuit to enter a low current, nerve node finding mode, the circuit being further configured to enter a high current therapeutic voltage pulse mode when a nerve node is found and to automatically shut off when a dose of therapeutic voltage pulses have been delivered.

According to an embodiment, the therapeutic electrode 1204 may be configured to maximize comfort for the user. This may be accomplished by keeping a diameter and radius of the therapeutic electrode 1204 tip at the forward end 1208 of the case large enough to avoid applying undue pressure against the user's skin. The inventors have found that maximizing the diameter and radius for comfort should be balanced against localization of current flow across the user's skin. In an embodiment, the exposed portion of the therapeutic electrode 1204 may have a diameter greater than or equal to 1/16 of an inch (0.0625") (1/32"=0.031" radius) and less than 1/4" (0.25") diameter (1/8"=0.125" radius). In another embodiment, the exposed portion of the therapeutic electrode 1204 may have a diameter greater than or equal to 3/32" (=0.094") (3/64"=0.047") and less than or equal to 3/16" (0.188") diameter and 3/32"=0.094" radius. In another embodiment, the exposed portion of the therapeutic electrode 1204 may have a diameter equal to about 5/32" (0.16") and 5/64" (0.078" radius). Relevant dimensions, according to an embodiment, are shown in FIG. 5.

According to embodiments, the inventors have noted three primary ways users may hold the device:

1. Thumb directed—the user puts his/her thumb in the indentation and points toward the user's face. The user's fingers wrap around the hand holdable case 1206.

2. Finger directed—the user places his/her index finger on the tapered surface 1216 and points toward the user's face. The user's fingers and thumb wrap around the hand holdable case 1206.

3. Hybrid—the user places his/her thumb on the indentation and places his/her index finger on the side, both thumb and index finger point toward the user's face. The user's middle finger stabilizes along the front. (Some users were found to be unable to use this technique.)

All three approaches are amenable to right-handed or left-handed use. Users naturally fell into one of the three grips. Features on the hand holdable case 1206 enable one or more of the grips.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A microcurrent sinus treatment device comprising:
a circuit configured to deliver a sequence of voltage pulses carrying a therapeutic current;
a therapeutic electrode operatively coupled to the circuit, the therapeutic electrode being configured to apply the sequence of voltage pulses to a user's facial skin surface, the therapeutic electrode being in electrical continuity with a therapeutic current output node of the circuit; and
a hand holdable case substantially containing portions of the circuit, the hand holdable case including:
a forward end terminating in the therapeutic electrode;
a resilient member coupled to the therapeutic electrode and configured to enable the therapeutic electrode to resiliently depress into the hand holdable case along an approximately longitudinal direction of the hand holdable case when force is applied to the therapeutic electrode and to return to an equilibrium position when the force is removed;
a return electrode comprising a portion of or disposed on a surface of the hand holdable case, the return electrode being in electrical continuity with a current return node of the circuit;
a dielectric spacer disposed between the therapeutic electrode and the return electrode; and
a rearward portion of the hand holdable case terminating at an end distal to the therapeutic electrode;
wherein the dielectric spacer and the return electrode form a tapered surface narrowing toward the therapeutic electrode from a point of maximum girth disposed between the forward end and the rearward portion of the hand holdable case, and
wherein the circuit is configured to perform steps of:
detecting, in a detection mode, an impedance level through a user's body between the therapeutic electrode of the sinus treatment device and the return electrode of the sinus treatment device as the therapeutic electrode is placed at various locations on the user's facial skin surface;
when the detected impedance level through the user's body is below a threshold impedance at a present location of detection, causing the sinus treatment device, if in the detection mode, to automatically enter a treatment mode, the treatment mode starting by gradually increasing, over a plurality of pulses of the sequence of voltage pulses, a current magnitude of the therapeutic current up to a predetermined current magnitude;
after reaching the predetermined current magnitude of the therapeutic current, adjusting the current magnitude of the therapeutic current to maintain a constant therapeutic current at or below the predetermined current magnitude until a predetermined criterion is satisfied, the treatment mode further including, when the predetermined current magnitude is reached, passing the therapeutic current at a magnitude averaging less than 1000 µA over a resistive load of 10KΩ to 100KΩ through the user's body between the therapeutic electrode and the return electrode; and automatically returning to the detection mode when the circuit detects that the detected impedance is greater than the threshold impedance.

2. The microcurrent sinus treatment device of claim 1, wherein the circuit is configured such that the therapeutic current includes a series of current spikes.

3. The microcurrent sinus treatment device of claim 2, wherein the circuit is configured such that:

gradually increasing the magnitude of the therapeutic current includes gradually increasing an amplitude of successive current spikes; and the circuit ceases increasing the magnitude of the therapeutic current when the current spikes reach the predetermined current magnitude.

4. The microcurrent sinus treatment device of claim 3, wherein the circuit is configured such that, after reaching the predetermined current magnitude, subsequent current spikes each have a magnitude substantially equal to the predetermined current magnitude.

5. The microcurrent sinus treatment device of claim 2, wherein the circuit is configured such that the series of current spikes have a peak magnitude of less than 1000 µA.

6. The microcurrent sinus treatment device of claim 5, wherein the circuit is configured such that the current spikes have a peak magnitude of less than 600 µA.

7. The microcurrent sinus treatment device of claim 5, wherein the circuit is configured such that the current spikes have an average value less than 600 µA.

8. The microcurrent sinus treatment device of claim 2, wherein the circuit is configured such that the current spikes alternate between positive and negative values.

9. The microcurrent sinus treatment device of claim 8, wherein the circuit is configured such that the current spikes alternate at a frequency less than 1000 Hz.

10. The microcurrent sinus treatment device of claim 9, wherein the circuit is configured such that the current spikes alternate at a frequency between 1 Hz and 100 Hz.

11. The microcurrent sinus treatment device of claim 2, wherein the circuit is configured such that the current spikes make up less than 10% of a single cycle during the treatment mode.

12. The microcurrent sinus treatment device of claim 11, wherein the circuit is configured such that the current spikes make up less than 5% of a single cycle during the treatment mode.

13. The microcurrent sinus treatment device of claim 1, wherein the circuit is configured such that the therapeutic current has a zero DC offset.

14. The microcurrent sinus treatment device of claim 1, wherein the circuit is configured to apply the therapeutic current by applying a treatment stimulation voltage between the therapeutic electrode and the return electrode.

15. The microcurrent sinus treatment device of claim 1, wherein the circuit is configured such that the sinus treatment device applies the therapeutic current by applying a treatment stimulation voltage between the therapeutic electrode and the return electrode, wherein the circuit is further configured to:

adjust the treatment stimulation voltage as the impedance changes between the therapeutic electrode conductive tip and the return electrode during the treatment mode; and maintain the therapeutic current at a substantially constant magnitude during the treatment mode by adjusting the stimulation voltage responsive to changes in the impedance during the treatment mode.

16. The microcurrent sinus treatment device of claim 1, wherein the circuit is configured such that the therapeutic current has a magnitude less than 600 µA.

17. The microcurrent sinus treatment device of claim 16, wherein the circuit is configured such that the therapeutic current alternates between positive and negative current values.

18. The microcurrent sinus treatment device of claim 1, wherein the circuit is configured to provide haptic feedback to the user's body during the treatment mode.

19. The microcurrent sinus treatment device of claim 1, wherein relative placements of the therapeutic electrode, the dielectric spacer, and the return electrode are configured to cause the user's body to complete a circuit between the therapeutic electrode and the return electrode.

20. The microcurrent sinus treatment device of claim 1, wherein the hand holdable case forms a surface having an indentation structured and oriented to receive the user's thumb, when the hand holdable case is gripped by the user, on a back side of the hand holdable case such that a front portion of the indentation extends toward the therapeutic electrode and away from the point of maximum girth of the hand holdable case.

21. The microcurrent sinus treatment device of claim 1, wherein the hand holdable case defines a tapered surface on a top, between the point of maximum girth and the forward end, configured to provide a finger hold.

22. The microcurrent sinus treatment device of claim 1, wherein the hand holdable case defines a convex curved surface, on the top between the point of maximum girth and the rearward portion, configured to fit into a hollow of the user's palm.

23. The microcurrent sinus treatment device of claim 1, further comprising a button configured to cause the circuit to enter the detection mode, the circuit being further configured to automatically shut off when a predetermined dose of therapeutic voltage pulses has been delivered.

24. The microcurrent sinus treatment device of claim 1, wherein an exposed portion of the therapeutic electrode has a round cross-section having a radius of curvature of greater than or equal to 0.031 inch and less than or equal to 0.25 inch.

25. The microcurrent sinus treatment device of claim 1, wherein the exposed portion of the therapeutic electrode is formed from stainless steel.

* * * * *